United States Patent
Asogawa et al.

(10) Patent No.: US 10,286,395 B2
(45) Date of Patent: May 14, 2019

(54) MICROCHIP, MICROCHIP CONTROLLING METHOD AND MICROCHIP CONTROLLING APPARATUS

(71) Applicant: NEC Corporation, Minato-ku, Tokyo (JP)

(72) Inventors: Minoru Asogawa, Tokyo (JP); Yoshinori Mishina, Tokyo (JP); Hisashi Hagiwara, Tokyo (JP); Yasuo Iimura, Tokyo (JP)

(73) Assignee: NEC CORPORATION, Tokyo (JP)

( * ) Notice: Subject to any disclaimer, the term of this patent is extended or adjusted under 35 U.S.C. 154(b) by 80 days.

(21) Appl. No.: 15/127,106

(22) PCT Filed: Mar. 19, 2015

(86) PCT No.: PCT/JP2015/058288
§ 371 (c)(1),
(2) Date: Sep. 19, 2016

(87) PCT Pub. No.: WO2015/141790
PCT Pub. Date: Sep. 24, 2015

(65) Prior Publication Data
US 2017/0106369 A1    Apr. 20, 2017

(30) Foreign Application Priority Data
Mar. 20, 2014 (JP) ................. 2014-058230

(51) Int. Cl.
*B01L 3/00* (2006.01)
*C12N 15/10* (2006.01)
*F16K 99/00* (2006.01)

(52) U.S. Cl.
CPC ..... *B01L 3/502738* (2013.01); *B01L 3/50273* (2013.01); *C12N 15/1003* (2013.01);
(Continued)

(58) Field of Classification Search
CPC .. B01L 3/502707; B01L 3/5027; B01L 3/502; B01L 3/50; F16K 99/0001; F16K 99/00
(Continued)

(56) References Cited

U.S. PATENT DOCUMENTS 6,619,311 B2    9/2003    O'Connor et al.
8,623,294 B2    1/2014    Asogawa et al.
(Continued)

FOREIGN PATENT DOCUMENTS

GB    2453310 A    4/2009
JP    2010-008190 A    1/2010
(Continued)

OTHER PUBLICATIONS

Extended European Search Report for EP Application No. EP15765832.9 dated Aug. 21, 2017.
(Continued)

*Primary Examiner* — Christine T Mui

(57) ABSTRACT

A microchip comprises a plurality of laminated elastic sheets, wherein the elastic sheets are partially inadhesive each other so that at least 3 middle layers are formed; as a first middle layer, first flow path and second flow path through which liquid flows are formed; as a second middle layer, a first flow path opening/closing section for opening and closing the first flow path is formed; and as a third middle layer, a second flow path opening/closing section for opening and closing the second flow path is formed.

14 Claims, 19 Drawing Sheets

(52) U.S. Cl.
CPC ............... *B01L 2300/0816* (2013.01); *B01L 2300/0887* (2013.01); *B01L 2300/123* (2013.01); *B01L 2400/0481* (2013.01); *B01L 2400/0622* (2013.01); *B01L 2400/0655* (2013.01); *F16K 2099/008* (2013.01); *F16K 2099/0084* (2013.01)

(58) Field of Classification Search
USPC .................. 422/68.1, 50, 240, 255, 243
See application file for complete search history.

(56) References Cited

U.S. PATENT DOCUMENTS

| | | | |
|---|---|---|---|
| 8,741,231 | B2 | 6/2014 | Asogawa et al. |
| 2002/0166585 | A1* | 11/2002 | O'Connor ............. B01L 3/5025 137/87.01 |
| 2002/0187560 | A1 | 12/2002 | Pezzuto et al. |
| 2003/0196695 | A1 | 10/2003 | O'Connor et al. |
| 2008/0057274 | A1* | 3/2008 | Hagiwara ......... B01L 3/502738 428/172 |
| 2009/0202391 | A1 | 8/2009 | Hagiwara et al. |
| 2010/0166609 | A1 | 7/2010 | Hasegawa et al. |
| 2011/0000561 | A1 | 1/2011 | Asogawa et al. |
| 2013/0273487 | A1 | 10/2013 | Asogawa et al. |
| 2013/0294980 | A1 | 11/2013 | Takahashi et al. |
| 2014/0079605 | A1 | 3/2014 | Asogawa et al. |

FOREIGN PATENT DOCUMENTS

| | | |
|---|---|---|
| JP | 2010-151717 A | 7/2010 |
| WO | 2009/119698 A1 | 10/2009 |
| WO | 2012/086168 A1 | 6/2012 |

OTHER PUBLICATIONS

International Search Report for PCT Application No. PCT/JP2015/058288, dated Jun. 2, 2015.

* cited by examiner

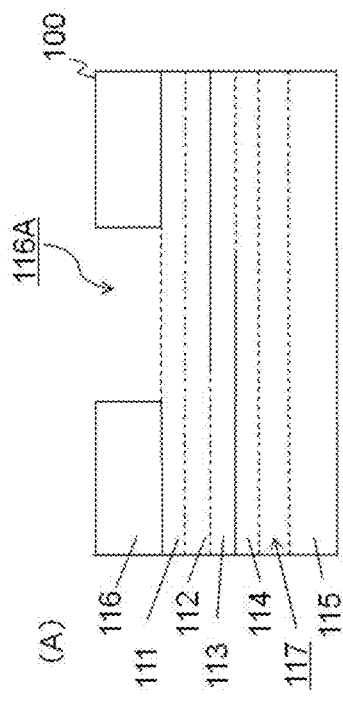
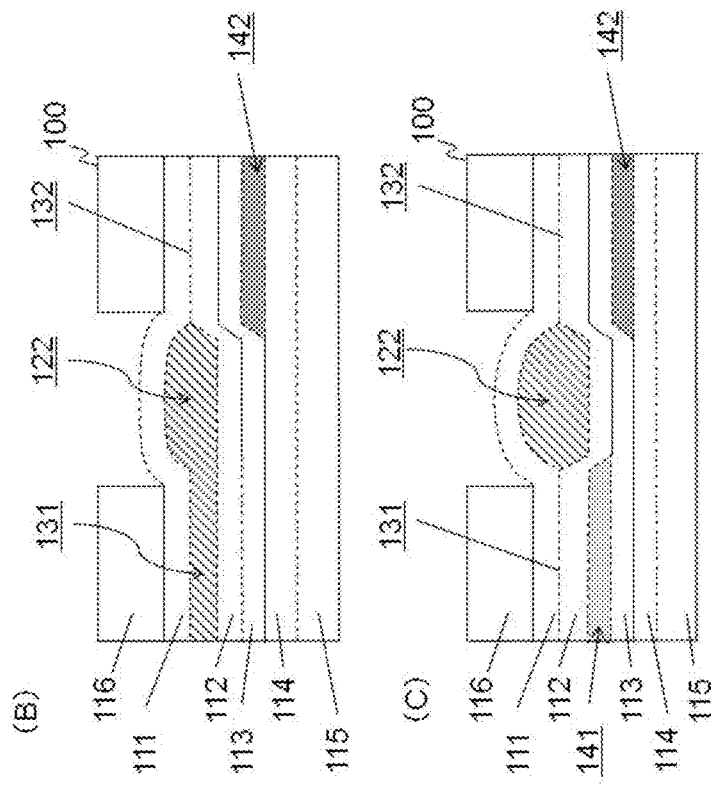
FIG. 3

MICROCHIP, MICROCHIP CONTROLLING METHOD AND MICROCHIP CONTROLLING APPARATUS

CROSS-REFERENCE TO RELATED APPLICATION

The present application is a National Stage Entry of PCT/JP2015/058288, filed on Mar. 19, 2015, which is based on and claims the benefits of priority of a Patent Application No. 2014-058230 filed in Japan on Mar. 20, 2014, the entire contents thereof being incorporated by reference into the present application.

TECHNICAL FIELD

The present invention relates to a microchip, microchip controlling method and microchip controlling apparatus.

BACKGROUND

Recently, technologies in which biochemical reaction, such as PCR (Polymerase Chain Reaction), is carried on a microchip have been developed. For example, Patent Literature 1 discloses a microchip consisting of laminated sheets (plates) comprising elastic member.

The microchip has a construction in which reaction chambers and flow paths may be formed between first sheet and second sheet by leaving inadhesive sites upon adhesion of the first sheet and second sheet. In addition, the microchip has a construction in which pressurization paths may be formed between the second sheet and third sheet.

Furthermore, Patent Literature 1 discloses a controlling apparatus controlling a microchip in a manner where upon liquid transfer between the reaction chambers, with respect to a flow path used for liquid transfer, a pressurization path is contracted by releasing pressurizing medium from the pressurization path in order to open a flow path; and with respect to the other flow paths, pressurization paths are expanded by injecting the pressurizing medium into the pressurization paths in order to close the flow paths.

Patent Literature 1

International publication No. 2009-119698A

SUMMARY

Analysis described below is made from an aspect of the present invention. Furthermore, Patent Literature is incorporated into this application by citation.

A problem in the microchip disclosed in Patent Literature 1 will be explained with reference to FIGS. 18 and 19. As shown in FIG. 18A, in a case where pressurization paths A to C for flow paths A to C do not extend to edge of a reaction chamber, liquid reagent remains in the flow path A even after that the liquid flows from the flow path A into the reaction chamber and, furthermore the liquid flows from the reaction chamber into the flow paths B, C. Therefore, as shown in FIG. 18B, it is preferable that the pressurization paths A to C extend to the edge of the reaction chamber.

However, in a case where the pressurization paths extend to the edge of the reaction chamber, the number of flow paths which may be connected to the reaction chamber is significantly restricted. Specifically, as shown in FIG. 19A, if it is desired to add an additional flow path, there would be a case where an existing pressurization path overlaps with a region where new pressurization path is arranged, resulting in that the flow path cannot be added. Furthermore, as shown in FIG. 19B, even in a case where a flow path may be added, distance between pressurization paths is shortened together with increment in the number of the flow paths, resulting in that adhesion between the sheets may be easily peeled off to generate communication between the pressurization paths.

Accordingly, the microchip disclosed in Patent Literature 1 has a problem that there are many restrictions in the number of flow paths and their arrangement, thus the flow paths cannot be designed freely. Therefore, it is a purpose of the present invention to provide a microchip, microchip controlling method and microchip controlling apparatus which have excellent flexibility in design of flow paths.

According to one aspect of the present invention, there is provided a microchip comprising a plurality of laminated elastic sheets, wherein the elastic sheets are partially inadhesive each other so that at least 3 middle layers are formed; as a first middle layer, first flow path and second flow path through which liquid flows are formed; as a second middle layer, first flow path opening/closing section for opening and closing the first flow path is formed; and as a third middle layer, second flow path opening/closing section for opening and closing the second flow path is formed.

In addition, according to another aspect of the present invention, there is provided a microchip controlling method, in which a microchip comprises a plurality of laminated elastic sheets; in which the elastic sheets are partially inadhesive each other so that at least 3 middle layers are formed; in which, as a first middle layer, a first flow path and second flow path through which liquid flows are formed, as a second middle layer, a first flow path opening/closing section for opening and closing the first flow path is formed; and in which, as a third middle layer, a second flow path opening/closing section for opening and closing the second flow path is formed; wherein, when liquid flows through the first flow path, medium is released from the first flow path opening/closing section so that the first flow path opening/closing section shrinks in order to open the first flow path, and medium is injected into the second flow path opening/closing section so that the second flow path opening/closing section is expanded in order to close the second flow path.

In addition, according to another aspect of the present invention, there is provided a microchip controlling apparatus: in which the microchip comprises a plurality of laminated elastic sheets; in which the elastic sheets are partially inadhesive each other so that at least 3 middle layers are formed; in which, as a first middle layer, first flow path and second flow path through which liquid flows are formed, in which, as a second middle layer, a first flow path opening/closing section for opening and closing the first flow path is formed; and in which, as a third middle layer, a second flow path opening/closing section for opening and closing the second flow path is formed; wherein, when liquid flows through the first flow path, medium is released from the first flow path opening/closing section so that the first flow path opening/closing section shrinks in order to open the first flow path, and medium is injected into the second flow path opening/closing section so that the second flow path opening/closing section is expanded in order to close the second flow path.

According to each aspect of the present invention, there is provided a microchip, microchip controlling method and microchip controlling apparatus which have excellent flexibility in design of flow paths.

BRIEF DESCRIPTION OF THE DRAWINGS

FIG. 3 is a summary diagram showing a microchip 100.

PREFERRED MODES

Figure 1:
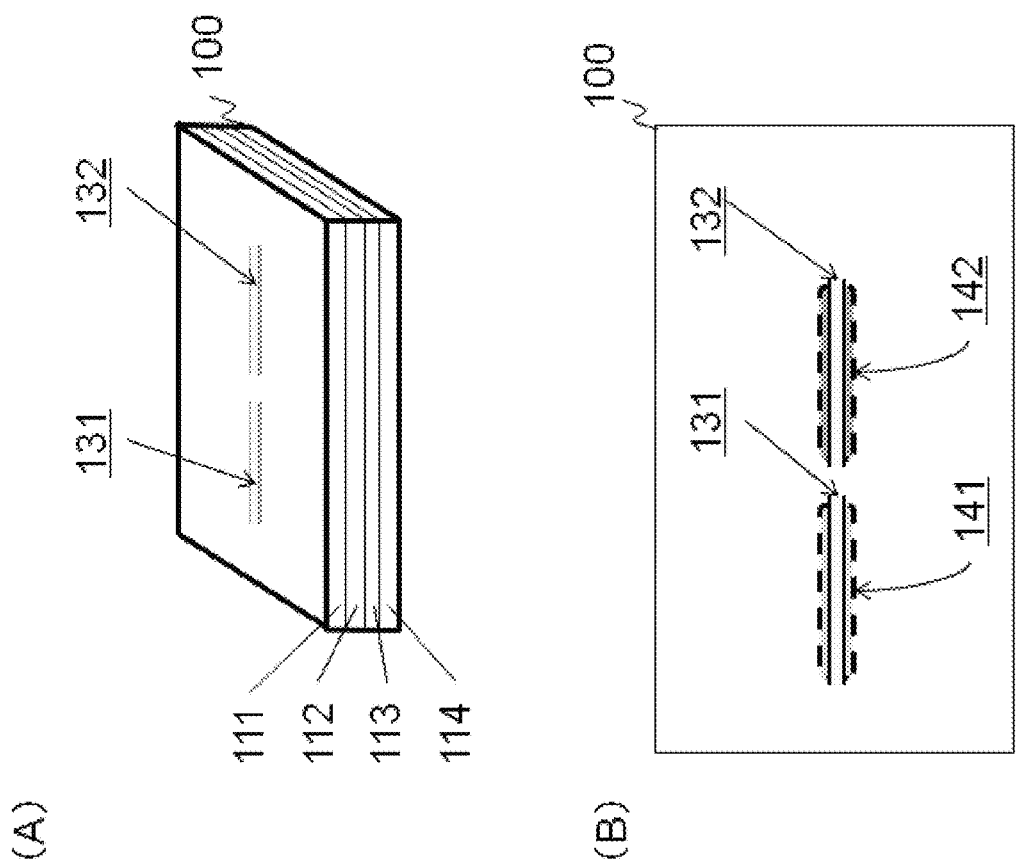
FIG. 1 is a summary diagram showing a microchip 100.

Preferable embodiments will be explained in detail below with reference to drawings. It should be noted that it is not intended to be limited to the mode shown in the drawings. In addition, symbols are merely attached for convenience in understanding the explanation.

In first, summary of a microchip 100 will be explained with reference to FIG. 1. As shown in FIG. 1, the microchip 100 comprises a plurality of laminated elastic sheets 111 to 114. The elastic sheets are partially inadhesive each other so that at least 3 middle layers are formed. In addition, as a first middle layer, first flow path 131 and second flow path 132 through which liquid flows are formed; as a second middle layer, a first flow path opening/closing section 141 for opening and closing the first flow path 131 is formed; and as a third middle layer, a second flow path opening/closing section 142 for opening and closing the second flow path 132 is formed. Herein, FIG. 1A is a perspective view of the microchip 100, conceptionally showing the flow paths 131, 132. FIG. 1B is a conceptual view of the first middle layer, in which broken line means each construction arranged as the second middle layer and the third middle layer.

Figure 2:
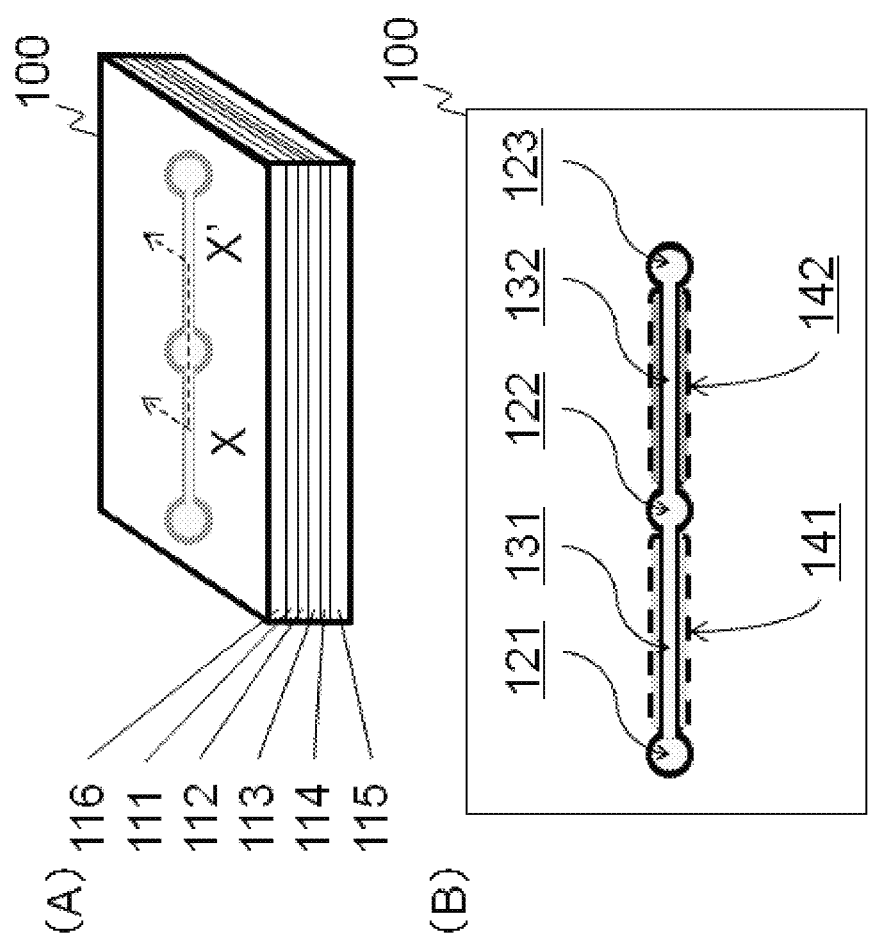
FIG. 2 is a summary diagram showing a microchip 100.

In a specific example, as shown in FIG. 2A, the microchip 100 is consisting of laminated first elastic sheet 111, second elastic sheet 112, third elastic sheet 113, fourth elastic sheet 114, and resin plates 115, 116. Specifically, in the microchip 100, the fourth elastic sheet 114 is superposed on the resin plate 115, the third elastic sheet 113 is superposed on the fourth elastic sheet 114, the second elastic sheet 112 is superposed on the third elastic sheet 113, the first elastic sheet 111 is superposed on the second elastic sheet 112, and the resin plate 116 is superposed on the first elastic sheet 111.

The elastic sheets 111 to 114 are partially inadhesive so that at least 3 middle layers are formed. That is, the inadhesive sites may be expanded by injection of liquid or gas, at that time, the middle layers are formed between the elastic sheets 111 to 114. Herein, the middle layer between the first elastic sheet 111 and the second elastic sheet 112 is referred to as first middle layer, the middle layer between the second elastic sheet 112 and the third elastic sheet 113 is referred to as second middle layer; and the middle layer between the third elastic sheet 113 and the fourth elastic sheet 114 is referred to as third middle layer.

In addition, as shown in FIG. 2B, on the microchip 100, liquid chambers 121 to 123 storing liquid and flow paths 131, 132 are formed as the first middle layer. The flow path 131 communicates the liquid chamber 121 with the liquid chamber 122, and the flow path 132 communicates the liquid chamber 122 with the liquid chamber 123. Furthermore, on the microchip 100, a flow path opening/closing section 141 is formed as the second middle layer, and a second flow path opening/closing section 142 is formed as the third middle layer. Herein, in FIG. 2A, the liquid chambers 121 to 123 and the flow paths 131, 132 are conceptionally shown. In addition, broken line in FIG. 2B means a construction arranged on lower layer of a construction indicated with full line.

Structure of each middle layer will be concretely explained with reference to FIGS. 3A to C as sectional view on X-X' indicated in FIG. 2A. As shown in FIG. 3A, before injection of medium, such as liquid or air, the microchip 100 comprises a space part 117 between the fourth elastic sheet 114 and the plate 115. In addition, the resin plate 116 is perforated at a site corresponding to the liquid chamber 122 to provide a control hole 116A into/from which pressurizing medium is injected/ejected. Broken line in FIG. 3 indicates inadhesive site. That is, the resin plate 116 and the first elastic sheet 111 are not adhered at a site corresponding to the liquid chamber 122, and the first elastic sheet 111 and the second elastic sheet 112 are not adhered at a site corresponding to the flow paths 131, 132 and the liquid chamber 122. In addition, the second elastic sheet 112 and the third elastic sheet 113 are not adhered at a site corresponding to the first flow path opening/closing section 141, and the third elastic sheet 113 and the fourth elastic sheet 114 are not adhered at a site corresponding to the second flow path opening/closing section 142. Furthermore, the fourth elastic sheet 114 and the resin plate 115 are not adhered at a site corresponding to the flow path opening/closing sections 141, 142. In a site shown in FIG. 3A, a space part 117 is interposed between the fourth elastic sheet 114 and the resin plate 115, thus being inadhesive.

FIG. 3B shows a situation in which liquid is currently flowing into the liquid chamber 122 through the flow path 131. That is, the second flow path opening/closing section 142 has been expanded by injection of pressurizing medium thereinto from outer section of the resin plate 116 so that the elastic sheet 114 is pressed down to contact to the resin plate 115. On the other hand, the elastic sheets 111 to 113 are under a pressed state onto the resin plate 116, resulting in that flow path 132 has been closed. In addition, the elastic sheets 112 to 114 has been pressed down by introduction of liquid into the flow path 131 and the liquid chamber 122. Therefore, the space part 117 in the FIG. 3A is disappeared in FIG. 3B.

FIG. 3C shows a state of resin plate 116 where liquid has flown into the liquid chamber 122. That is, the first flow path opening/closing section 141 is expanded by injection of pressurizing medium from outer section of the resin plate 116, resulting in that the flow path 131 is closed and liquid is accumulated in the liquid chamber 122.

Figure 4:
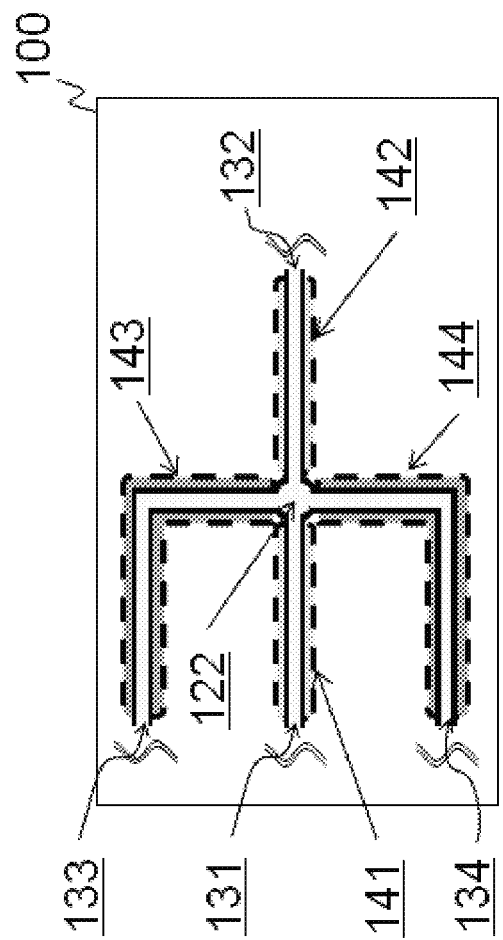
FIG. 4 is a summary diagram showing a microchip 100.

As apparent from FIG. 3C, in the microchip 100, the first flow path opening/closing section 141 is formed as the second middle layer, and the second flow path opening/closing section 142 is formed as the third middle layer. That is, the first flow path opening/closing section 141 and the second flow path opening/closing section 142 are formed as respective middle layers at different stage, and being separated with interposed third elastic sheet 113. Therefore, there is no possibility that adhesion between the elastic sheet is peeled off and the flow path opening/closing sections 141, 142 are to be communicated. In addition, in a case where new flow path connected to the liquid chamber 122 is added, flow path opening/closing sections for flow paths at a close distance may be formed as different middle layers. As shown in FIG. 4, for example, it may be realized in a manner where flow paths 131 to 134 connected to the liquid chamber 122 are radially arranged on periphery of the liquid chamber 122, flow path opening/closing sections 141, 142 for the flow paths 131, 132 arranged on diagonal line of the liquid chamber 122 are formed, and flow path opening/closing sections 143, 144 for the flow paths 133, 134 orthogonal to the flow paths 131, 132 are formed as different third middle layer. Or, it may be also realized in a manner where an additional fifth elastic sheet is added between the fourth elastic sheet 114 and the resin plate 115, and a flow path opening/closing section for the additional flow path is formed as a middle layer between the fourth elastic sheet and the fifth elastic sheet.

Accordingly, in the microchip 100 of an exemplary embodiment, a flow path may be added without concerning overlap of flow path opening/closing sections, and there is no bad effect that communication between flow path opening/closing sections are easily generated due to addition of a flow path. That is, the microchip 100 has an excellent flexibility in design of the flow paths.

First Embodiment

Figure 5:
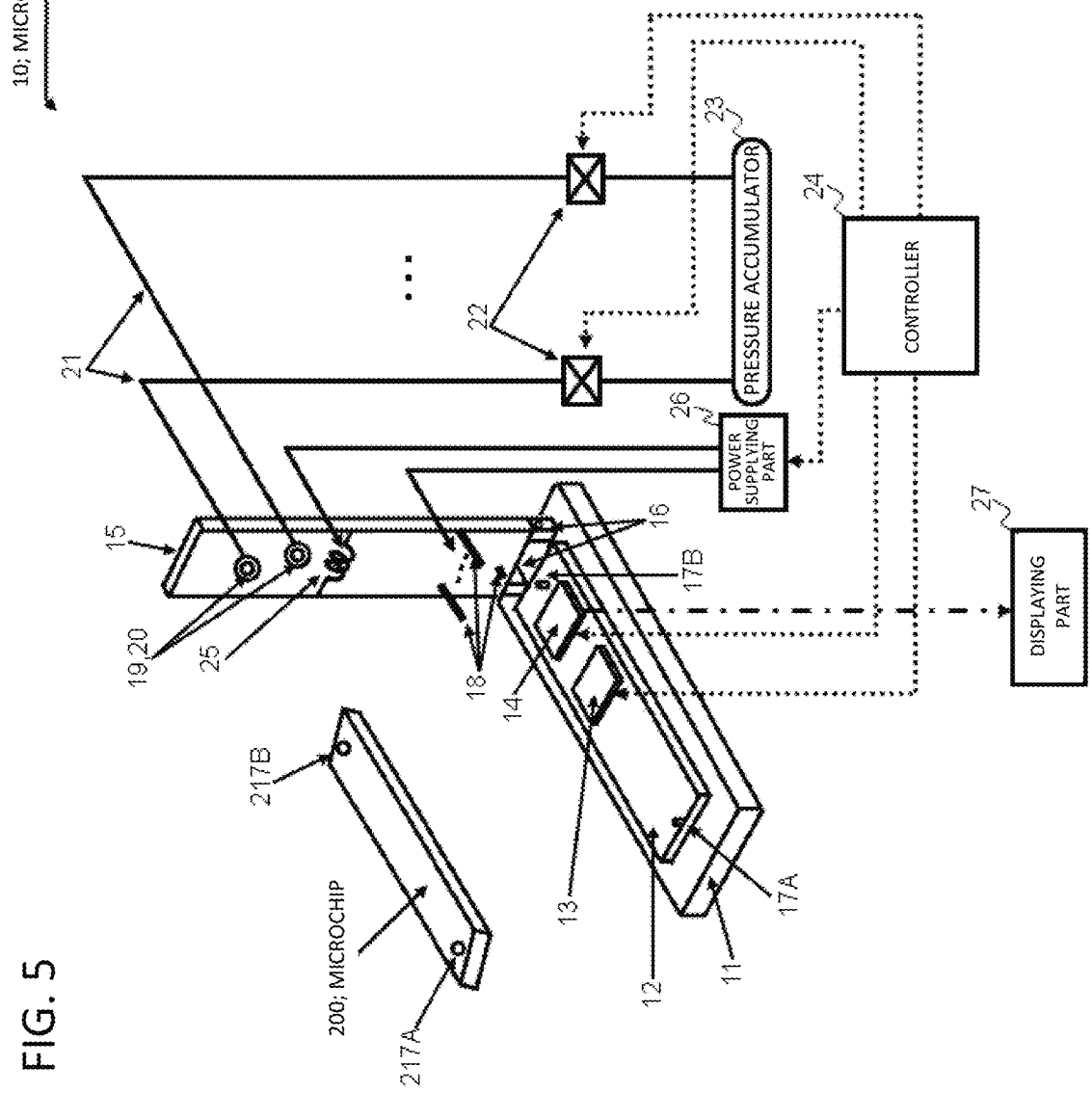
FIG. 5 is an exemplary view showing a microchip controlling apparatus 10.

A microchip and controlling method thereof will be exemplified and explained below with reference to drawings. A microchip 200 shown in FIG. 5 is an example of the microchip 100 shown in FIGS. 1 to 4, which is for carrying out DNA (deoxyribonucleic acid) analysis (PCR and electrophoresis). In the microchip controlling apparatus 10, a table 12 is arranged on a base station 11, and a temperature control unit 13 and an electrophoresis unit 14 are arranged on the table 12. In addition the base station 11 and a lid 15 are jointed with a hinge 16 so that the lid 15 may be opened and closed.

The microchip 200 is placed on a predetermined position on the table 12 by engaging pin 17A and pin 17B arranged on the table 12 with pin holes 217A and 217B arranged on the microchip 200. When the lid 15 is closed in a condition where the microchip 200 has been placed on the table 12, a PCR section 245 and a denaturation section 246 of the microchip 200 contacts to the temperature control unit 13. In addition, by closing the lid 15, an electrophoresis section 280 contacts to surface of the electrophoresis unit 14 and electrodes 18 are inserted into electrode chambers 284 of sample flow paths 281 and capillary 282 via electrode holes arranged on the microchip 200.

A plurality of pressurizing holes 19 are arranged on the lid 15. Regions on the lid 15 corresponding to these pressurizing holes 19 are perforated, and the pressurizing holes 19 are communicated to a solenoid valve 22 via tubes 21. In addition, by closing the lid 15, the pressurizing holes 19 arranged on the lid 15 and a variety of control holes, such as medium charging/discharging holes 220, on the microchip 200 are connected. Herein, it is preferable that the pressurizing holes 19 and the control holes are brought into contact with an interposed sealing mechanism, such as O-rings 20 (see FIG. 8).

A pressure accumulator 23 stores pressurizing medium, such as compressed air, and a controller 24 controls a solenoid valve 22 so that pressurizing medium is injected into or ejected from the control holes (including medium charging/discharging holes 220) on the microchip 200 via the pressurizing holes 19. Herein, internal pressure in the pressure accumulator 23 is controlled by a pressure sensor, pump etc., not shown, so as to be maintained at a predetermined pressure. Herein, flow path opening/closing mechanism and liquid transferring mechanism by the microchip controlling apparatus 10 will be explained below.

A DNA extracting unit 25 is arranged on the lid 15, which extracts sample DNA from sample solution. In a case where the DNA extracting unit 25 extracts sample DNA with, for example, magnetic beads (silica), the DNA extracting unit 25 comprises neodymium magnets to which magnetic beads are attached. The DNA extracting unit 25 generates magnetic field at the DNA extracting section 244 on the microchip 200 by supplying power from a power supplying part 26. The controller 24 controls magnetization in the DNA extracting unit 25 by instructing the power supplying part 26 to supply power to DNA extracting unit 25 and terminate it. Herein, the DNA extraction methods are not restricted to the method in which magnetic beads are used, DNA may be extracted with silica bead column (for example, see QIAamp: QIAGEN Co., Ltd.).

The temperature control unit 13 has temperature controlling mechanism for carrying out PCR and denaturation process. Specifically, the temperature control unit 13 comprises a temperature sensor, heat conductor, Peltier element, heat releasing plate etc., which acquires temperature at the PCR section 245 and the denaturation section 246 from a temperature sensor, and controlling heating or cooling on the Peltier element based on the acquired temperature to achieve temperature control at the PCR section 245 and the denaturation section 246.

An electrophoresis unit 14 is a mechanism carrying out capillary electrophoresis and detection of fluorescent label, which comprises an excitation device, such as a halogen lamp, mercury lamp and laser beam, as well as a filter and camera. When capillary electrophoresis is initiated by applying DC voltage to the electrodes 18 via a power supplying part 26, the electrophoresis unit 14 monitors fluorescent label flowing in capillary and outputs detection result in which change in fluorescence intensity is graphed in a time dependent manner via a displaying part 27.

Figure 6:
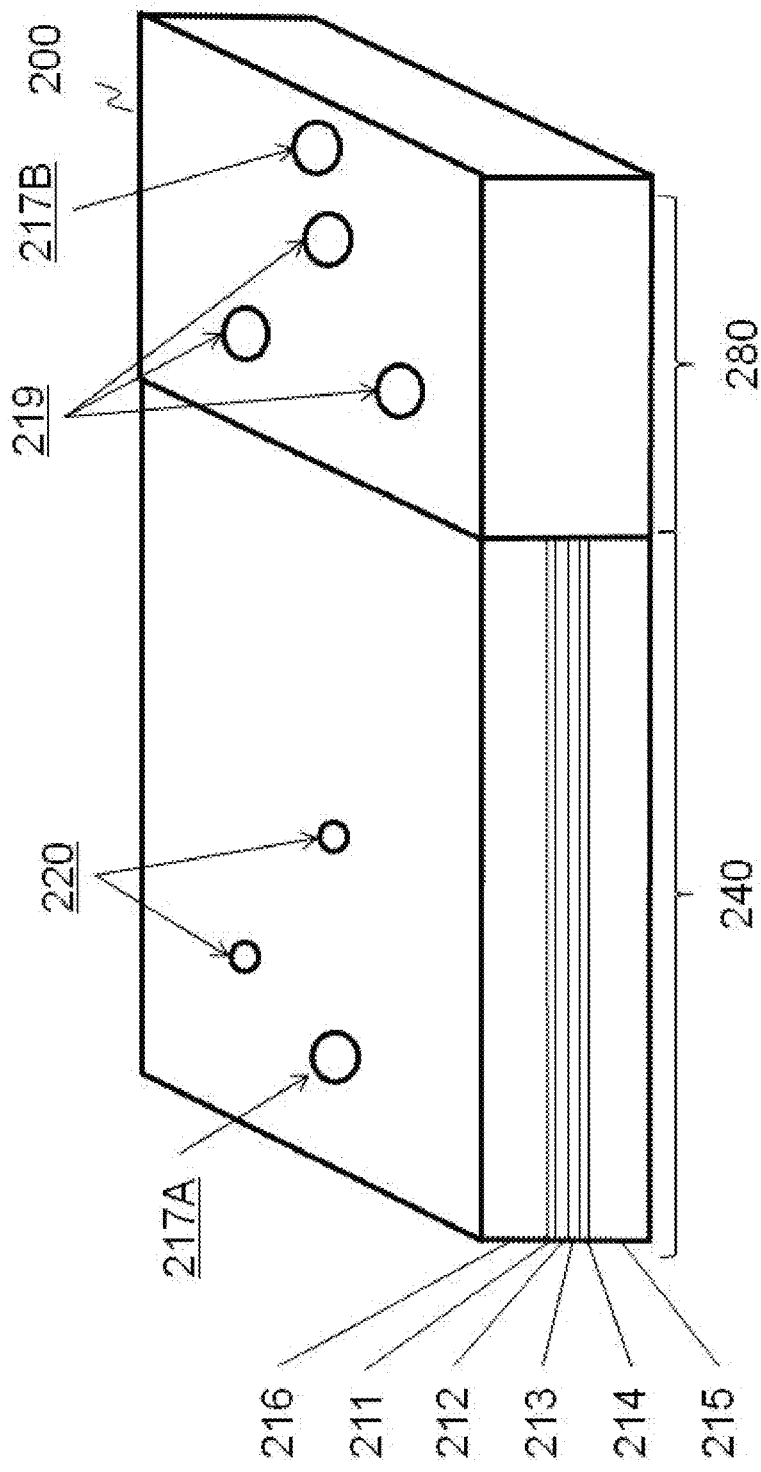
FIG. 6 is an exemplary view showing a microchip 200.

As shown in FIG. 6, the microchip 200 comprises a DNA extraction/PCR section 240 and electrophoresis section 280. The DNA extraction/PCR section 240 is consisting of fourth elastic sheet 214 superposed on a resin plate 215, third elastic sheet 213 superposed on the fourth elastic sheet 214, second elastic sheet 212 superposed on the third elastic sheet 213, first elastic sheet 211 superposed on the second elastic sheet 212, and a resin plate 216 superposed on the first elastic sheet 211. The elastic sheets 211 to 214 are adhered each other partial exceptions. Inadhesive site may be expanded by injection of medium, such as liquid and air, and then middle layer is formed between the elastic sheets 211 to 214. Herein, a middle layer between the first elastic sheet 211 and the second elastic sheet 212 is referred to as first middle layer, a middle layer between the second elastic sheet 212 and third elastic sheet 213 is referred to as second middle layer, and a middle layer between the third elastic sheet 213 and the fourth elastic sheet 214 is referred to as third middle layer.

It is preferable that the elastic sheets 211 to 214 have elasticity, heat resistance, and acid/alkali resistance. It is preferable that the resin plates 215, 216 have hardness to an extent such that they may control extension of the elastic sheets 211 to 214. Herein, the resin plate 215 may be also arranged on the base station 11 of the microchip controlling apparatus 10. A variety of control holes, such as a pin hole 217A and medium injecting/ejecting hole 220, are formed on the resin plate 216. In addition, a variety of control holes, such as pin hole 217B and electrode holes 219, are formed on the electrophoresis section 280. Note that FIG. 6 is partially simplified for clarity.

Figure 7:
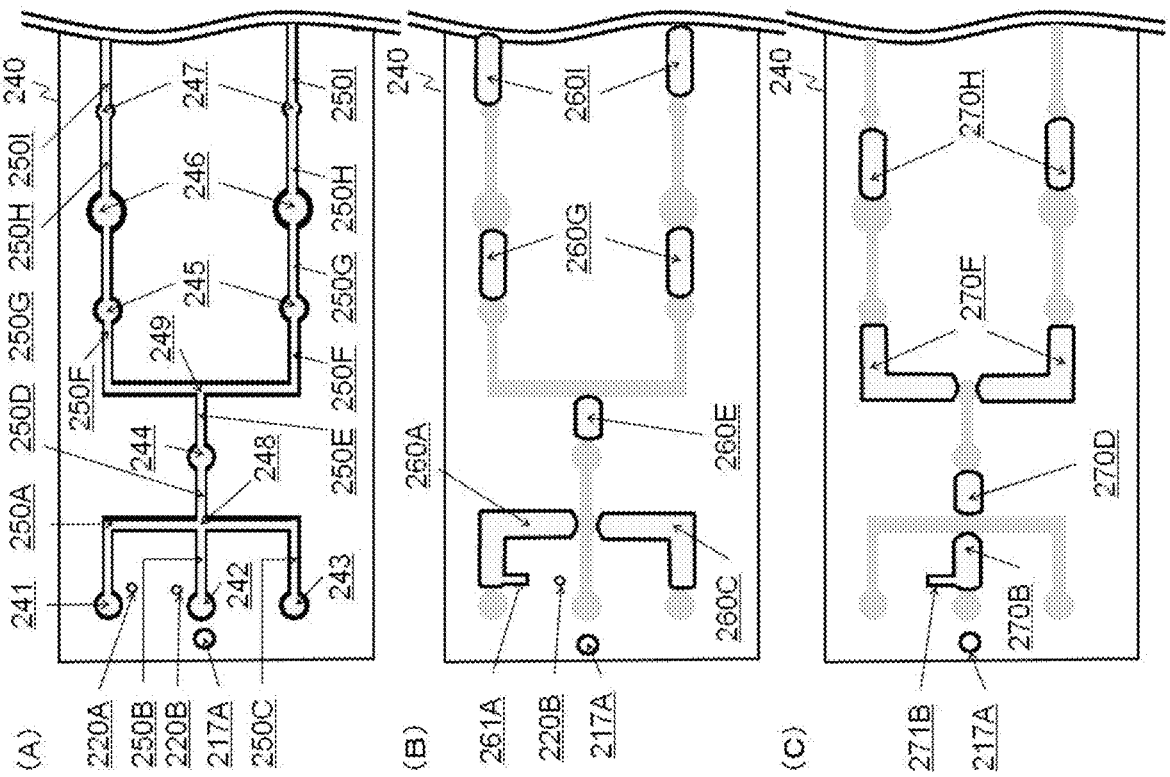
FIG. 7 is an exemplary view showing a DNA extraction/PCR section 240.

FIG. 7 is a conceptual view of the DNA extraction/PCR section 240. As shown in FIG. 7 (A), the DNA extraction/PCR section 240 comprises a sample solution injection section 241, wash buffer injection section 242 and elution buffer injection section 243, in which DNA extracting section 244, PCR section 245, denaturation section 246 and volume determination section 247 are formed as first middle layer. In addition, the DNA extracting section 244 is also connected to flow path 250E. The flow path 250E branches at a branching point 249 and being communicated with a plurality of PCR sections 245 as flow path 250F. Each PCR section 245 is respectively communicated with a corresponding denaturation section 246 via a flow path 250G and communicated with a volume determination section 247 from the denaturation section 246 via a flow path 250H. The volume determination section 247 is communicated with the electrophoresis section 280 via a flow path 250I. Herein, the flow paths 250 and the like are inadhesive site between the first elastic sheet 211 and the second elastic sheet 212, which are formed by injection of liquid etc. thereinto. That is, space section 290 is arranged between the fourth elastic sheet 214 and the resin plate 215. Upon formation of the flow path 250 and the like, the elastic sheet 214 is pressed down into the space section 290 (see FIG. 8 and FIG. 9).

As shown in FIG. 7B, flow path opening/closing sections 260A, C, E, G, I corresponding to the flow paths 250A, C, E, G, I are formed on the DNA extraction/PCR section 240 as second middle layer between the second elastic sheet 212 and the third elastic sheet 213. In addition, as shown in FIG. 7C, flow path opening/closing sections 270B, D, F, H corresponding to the flow paths 250B, D, F, H are formed as third middle layer between the third elastic sheet 213 and the fourth elastic sheet 214.

As shown in FIG. 7B, the flow path opening/closing section 260A comprises medium flow path 261A at upstream side of the flow path 250A (that is, the side of the sample solution injection section 241) and being connected to a pressurizing hole 19 arranged on the lid 15 via a medium injecting/ejecting hole 220A through the first middle layer, first elastic sheet 211 and resin plate 216. In addition, as shown in FIG. 7C, the flow path opening/closing section 270B comprises medium flow path 271B at upstream side of the flow path 250B (that is, the side of the wash buffer injection section 242) and being connected to a pressurizing hole 19 arranged on the lid 15 via a medium injecting/ejecting hole 220B through the second middle layer, second elastic sheet 212, first middle layer, first elastic sheet 211 and resin plate 216. Herein, only the medium flow path 261A, medium injecting/ejecting hole 220A, medium flow path 271B and medium injecting/ejecting hole 220B are shown in FIG. 7, and the other constructions are omitted.

Figure 8:
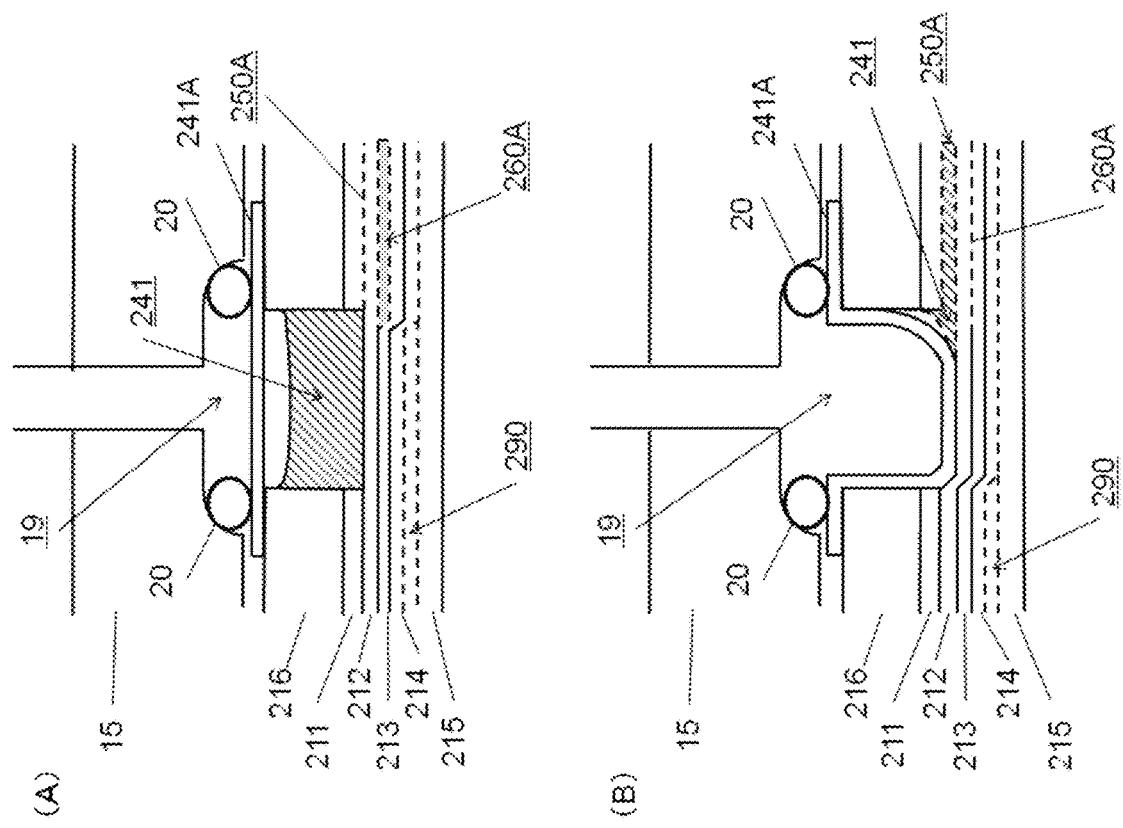
FIG. 8 is an exemplary view showing a sample solution injection section 241.

As shown in FIG. 8, the sample solution injection section 241 is a through hole perforating the resin plate 216 and the first elastic sheet 211, into which sample solution is injected by an operator (manual operation or automatic injection means) and which is covered with a cover film 241A. The sample solution is solution in which cells obtained from a subject are suspended into lysis buffer (for example, SDS/LiOAc solution (sodium dodecyl sulfate/lithium acetate solution)). Specifically, the sample solution injection section 241 is connected to a pressurizing hole 19 arranged on the lid 15 via the cover film 241A and O-ring 20. Hereinafter, the pressurizing hole 19 is interpreted to comprise the O-ring 20, and explanation for the O-ring 20 would be omitted.

In a case where sample solution is transferred from the sample solution injection section 241 to the DNA extracting section 244 through the flow paths 250A, D, in first, the microchip controlling apparatus 10 injects pressurizing medium into the flow path opening/closing sections 260C, E and flow path opening/closing sections 270B so as to close flow paths 250B, C, E. Then flow paths 250A, D are opened by releasing pressurizing medium from the flow path opening/closing section 260A and flow path opening/closing section 270D. Then, as shown in FIG. 8B, the microchip controlling apparatus 10 applies pressurizing medium to the sample solution injection section 241 and presses down the cover film 241A so that the sample solution is extruded to the flow path 250A.

The wash buffer injection section 242 comprises similar construction with the sample solution injection section 241 excepting for that the flow path opening/closing section 270B corresponding to the flow path 250B is arranged as the third middle layer, into which wash buffer is injected by an operator. The wash buffer is, for example, Tris (tris (hydroxymethyl) aminomethane) buffer.

The elution buffer injection section 243 comprises similar construction with the sample solution injection section 241, into which elution buffer is injected by an operator. The elution buffer is buffer for elution of DNA from the DNA extracting section 244 (specifically, magnetic beads) and comprises polymerase for primer extension reaction.

Figure 9:
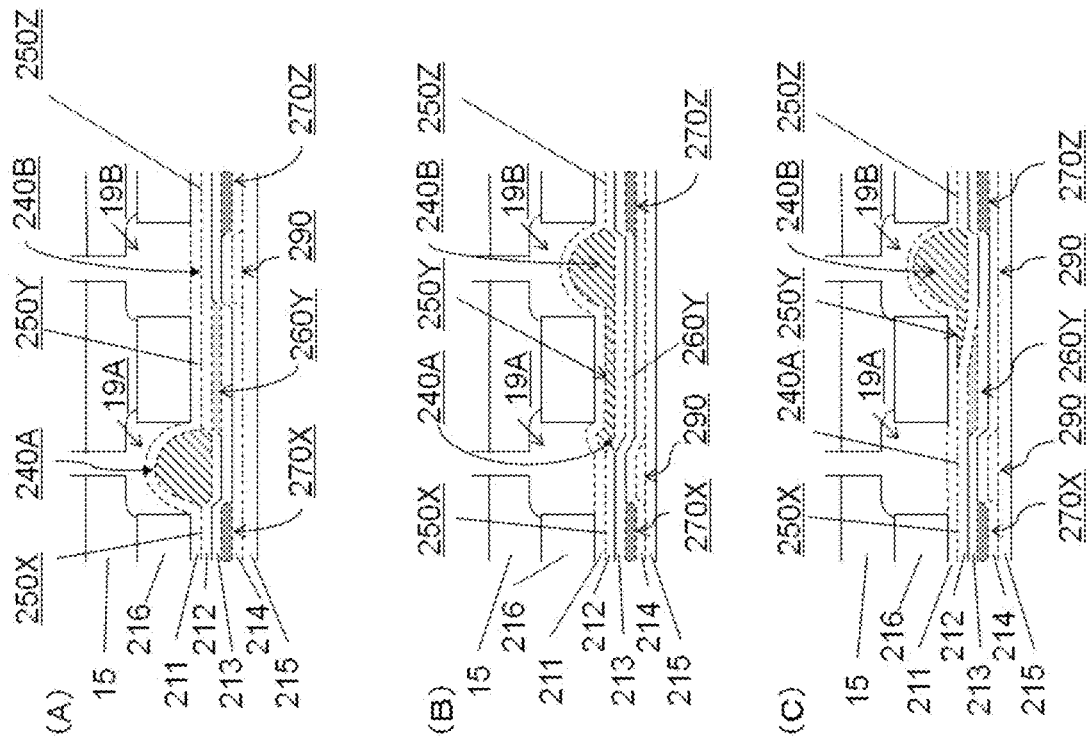
FIG. 9 is explanatory view of an example of liquid transferring mechanism on a microchip.
Figure 10:
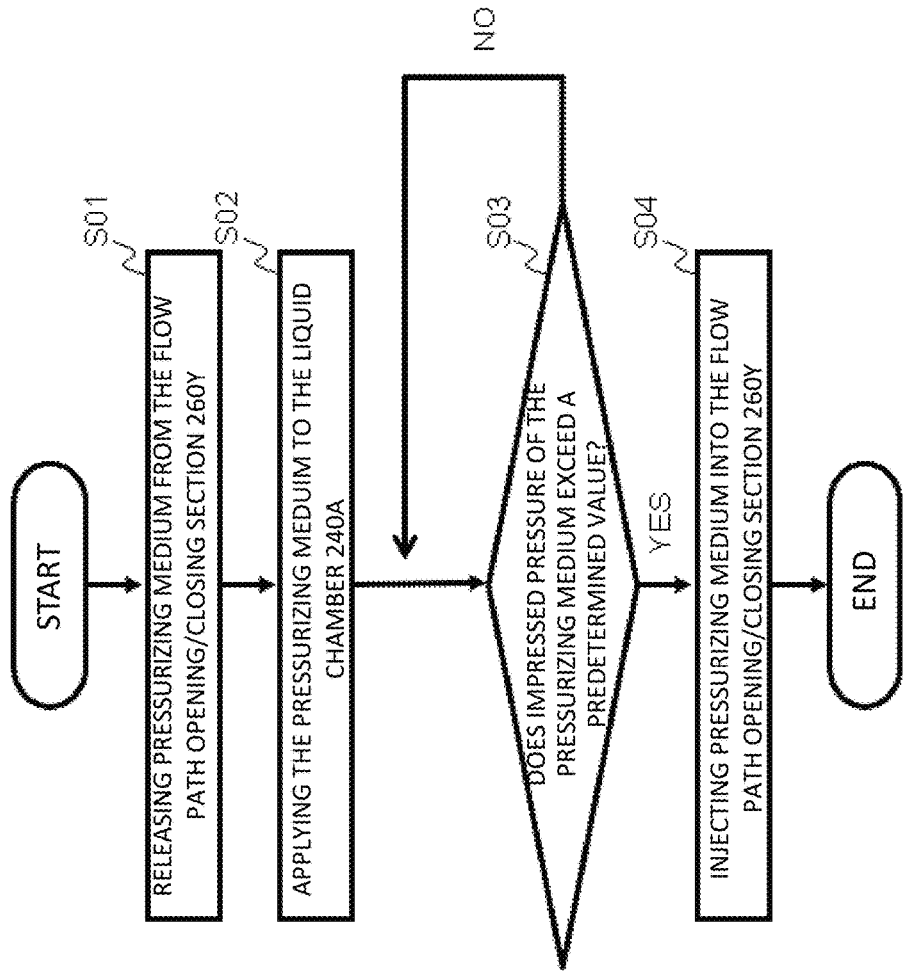
FIG. 10 is a flowchart showing an example of flow of opening/closing of flow path and liquid transfer by a microchip controlling apparatus 10.

Herein, flow path opening/closing mechanism and liquid transferring mechanism by the microchip controlling apparatus 10 will be explained. When liquid flows through the first flow path, the microchip controlling apparatus 10 opens the first flow path by releasing medium from the first flow path opening/closing section so as to contract the first flow path opening/closing section, and then closes the second flow path by injecting medium into the second flow path opening/closing section so as to expand the second flow path opening/closing section. Specifically, as shown in FIGS. 9, 10, liquid transferring mechanism in the microchip will be explained, in which liquid in a liquid chamber 240A is transferred to a liquid chamber 240B through a flow path 250Y. Herein, the DNA extracting section 244, PCR section 245, denaturation section 246, volume determination section 247 corresponds to "liquid chambers". As shown in FIG. 9A, the liquid chamber 240A is formed between the first elastic sheet 211 and the second elastic sheet 212 and being connected to flow paths 250X and 250Y. A part corresponding to the liquid chamber 240A on the resin plate 216 is perforated to form a control hole, and pressurizing medium may be injected into/ejected from upper section of the liquid chamber 240A through a pressurizing hole 19A arranged on the lid 15. Similarly, the liquid chamber 240B is connected to the flow paths 250Y and 250Z, and pressurizing medium may be injected into/ejected from upper section of the liquid chamber 240B. The flow paths 250X to Z are closed since pressurizing medium has been injected into the flow path opening/closing sections 270X, 260Y, 270Z (FIG. 10, before start).

Under such premise, in first, the microchip controlling apparatus 10 releases pressurizing medium from the flow path opening/closing section 260Y (FIG. 10, step S01) so as to open the flow path 250Y and applies the pressurizing medium to the liquid chamber 240A through the pressurizing holes 19A (FIG. 10, step S02). As a result, as shown in FIG. 9B, liquid extruded from the liquid chamber 240A reaches the liquid chamber 240B through the flow path 250Y, pushes up the first elastic sheet 211 and accumulates in the liquid chamber 240B. When the microchip controlling apparatus 10 determines that impressed pressure of pressurizing medium onto the liquid chamber 240A exceeds a predetermined value (FIG. 10, step S03, YES) and liquid has been ejected from the liquid chamber 240A, the microchip controlling apparatus 10, as shown in FIG. 7C [sic, FIG. 9C], injects pressurizing medium into the flow path opening/closing section 260Y from upstream side of the flow path 250Y (FIG. 10, step S04) (that is, the side of the liquid chamber 240A). As a result, liquid in the flow path 250Y is extruded into the liquid chamber 240B and the liquid transfer is completed.

Returning to explanation of FIG. 7, the DNA extracting section 244 is a mechanism arranged for extracting DNA from sample solution. For example, magnetic beads (silica) have been previously stored in the DNA extracting section 244 and DNA is extracted from sample solution according to control by the controller 24 and DNA extracting unit 25.

DNA extraction process will be concretely explained. The microchip controlling apparatus 10 comprises electromagnets as the DNA extracting unit 25 and magnetic beads coated with silica has been previously stored in the DNA extracting section 244. The microchip controlling apparatus 10 transfers sample solution injected into the sample solution injection section 241 to the DNA extracting section 244 so that sample DNA is attached on the magnetic beads (silica) stored in the DNA extracting section 244. Then, the magnetic beads are washed with wash buffer stored in the wash buffer injection section 242 so as to extract sample DNA. Herein, when the microchip controlling apparatus 10 discharges sample solution and wash buffer via a drainage port (not shown), magnetic beads are attached onto the electromagnets so that it is prevent that the magnetic beads are discharged together with the sample solution and wash buffer.

DNA extraction method may be modified with reference to a standard protocol etc., for example, rounds of washing may be increased. In addition, the DNA extraction method should not be limited to the method utilizing the magnetic beads, for example, a method utilizing column may be adopted.

The PCR section 245 carries out PCR. Specifically, a primer set is previously stored in the PCR section 245, the PCR section 245 receives temperature control by the temperature control unit 13 to carry out PCR. Specifically, the resin plate 215 is perforated at a site corresponding to the PCR section 245, a temperature control pin projecting from the temperature control unit 13 contacts with the PCR section 245 via the second elastic sheet. The primer set is a primer set for amplifying DNA at a predetermined microsatellite and the like, that is, for DNA test, condition in temperature control may be adjusted according to length of DNA and nucleic acid sequence as the purpose for amplification.

The denaturation section 246 carries out denaturation of amplicon into single-strand DNA. Specifically, the denaturation section 246 receives temperature control by the temperature control unit to heat solution containing amplicon in order to denature double-strand DNA into single-strand DNA. Herein, denaturation reagent, such as formamide, is able to be previously stored in or injected, if desired, into the denaturation section 246.

The volume determination section 247 is a mechanism for measuring solution comprising amplicon. Specifically, the volume determination section 247 is smaller than the denaturation section 246, upon liquid transfer between the denaturation section 246 and the volume determination section 247, the microchip controlling apparatus 10 closes the flow path 250H under a condition where transfer of solution in the denaturation section 246 to the volume determination section 247 has not been accomplished. In other words, the microchip controlling apparatus 10 leaves partial solution in the PCR section 245 so that desired volume of solution comprising amplicon is obtained.

Figure 11:
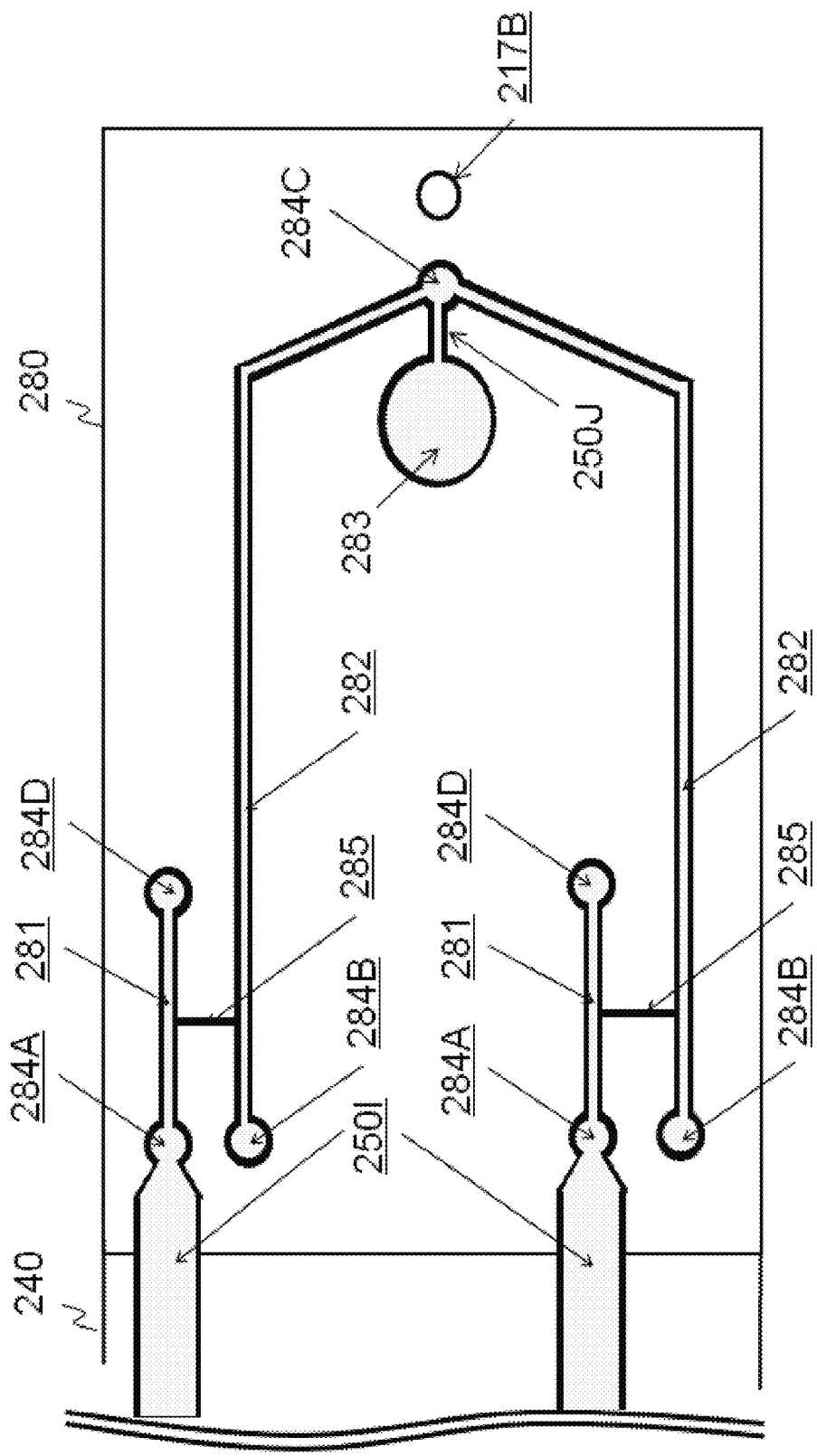
FIG. 11 is an exemplary view showing an electrophoresis section 280.

As shown in FIG. 11, the electrophoresis section 280 comprises sample flow paths 281, capillaries 282 and a polymer injection section 283. Specifically, the sample flow paths 281 are connected to the flow path 250I via electrode chambers 284A and whose edges at the side opposite to the flow path 250I are connected to the reservoirs 284D. The reservoirs 284D are a mechanism for preventing overflow of the sample flown into the sample flow path 281. The capillaries 282 are connected to electrode chambers 284B, C and the injection section 283 via a flow path 250J. In addition, the sample flow paths 281 and the capillaries 282 extend in parallel and being connected by bridge flow paths 285 orthogonal to the sample flow paths 281 and the capillaries 282. The electrodes 18 attached on the lid 15 are inserted into the electrode chambers 284A to C.

Sample injection into the capillaries 282 and capillary electrophoresis under such construction will be explained. The microchip controlling apparatus 10 injects pressurizing medium from the pressurizing hole 19 to compress the polymer injection section 283. As a result, polymer stored in the polymer injection section 283 moves to the capillaries 282 via the flow path 250J and the electrode chamber 284C.

Next, the microchip controlling apparatus 10 applies pressurizing medium to the volume determination section 247 so that the solution in the volume determination sections 247 moves to the sample flow paths 281. Finally, the solution fills up the sample flow paths 281 and reaches the reservoirs 284D, Then, the microchip controlling apparatus 10 applies pressurizing medium to the electrode chambers 284A and the reservoirs 284D so that the solution in the sample flow paths 281 is pressurized, and the microchip controlling apparatus 10 simultaneously applies pressurizing medium to the polymer injection section 283 and the electrode chambers 284B so that polymer in the capillary 282 is pressurized. As a result, solution in the sample flow paths 281 and polymer in the capillaries 282 flow into the bridge flow paths 285. At that time, air existing in the bridge flow paths 285 is discharged via an air permeable film and both end surfaces of the polymer and sample bring into contact to form interface.

Then, the microchip controlling apparatus 10 applies DC voltage between the electrode 18 inserted into the electrode chamber 284A and the electrode 18 inserted into the electrode chamber 284C and moves the amplicon in the sample flow path 281 to the capillary 282 in order to carry out sample injection.

After completion of sample injection, the microchip controlling apparatus 10 applies DC voltage between the electrode 18 inserted into the electrode chamber 284B and the electrode 18 inserted into the electrode chamber 284C in order to carry out electrophoresis. While the electrophoresis, the microchip controlling apparatus 10 monitors label flowing through the capillary with the electrophoresis unit 14 in order to output detection result via a displaying part 27, in which change in fluorescence intensity is graphed in a time dependent manner.

Figure 12:
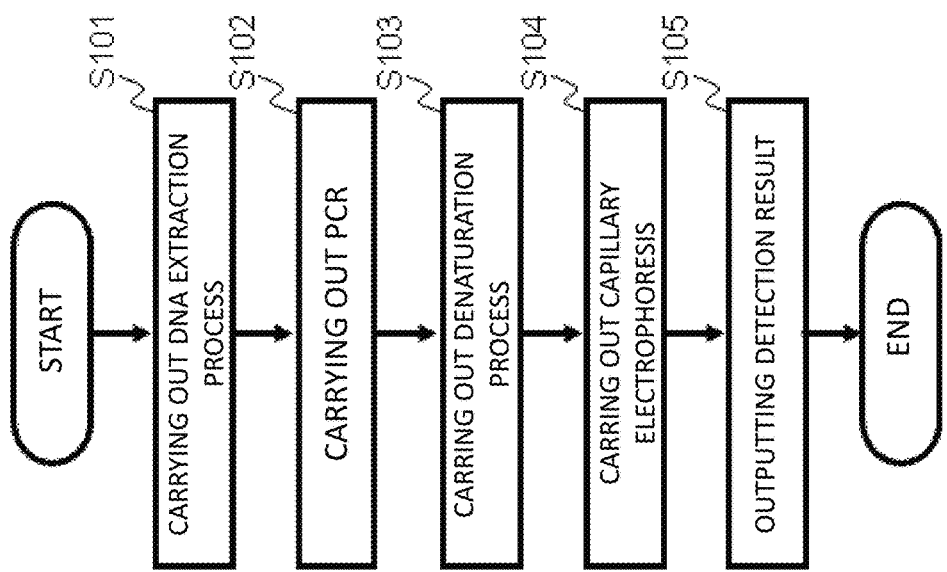
FIG. 12 is a flowchart showing an example of flow of DNA analysis process by a microchip controlling apparatus 10.

Next, flow of DNA analysis process by the microchip controlling apparatus 10 will be explained. Flow path opening/closing process and liquid transfer process by the microchip controlling apparatus 10 are omitted for simplifying explanation. In first, a microchip 200 filled up with sample solution, wash buffer, elution buffer and polymer. In first, a microchip 200 filled up with the sample solution, wash buffer, elution buffer and polymer is set on the microchip controlling apparatus 10 by a user. As shown in FIG. 12, the microchip controlling apparatus 10 carries out DNA extraction process in the DNA extracting unit 25 (step S101).

Then the microchip controlling apparatus 10 carries out PCR (step S102) and denaturation process (step S103) in the temperature control unit 13. In addition, the microchip controlling apparatus 10 carries out capillary electrophoresis and label detection process (step S104), and then outputs detection result via the displaying part 27 (step S105).

Accordingly, in the microchip 200, the flow path opening/closing sections 260, 270 are formed as the second middle layer and the third middle layer separated with elastic sheet, thus the microchip 200 has reduced the possibility that the flow path opening/closing sections 260, 270 are to be communicated. Particularly, it is preferable that the flow path opening/closing sections 260, 270 for the flow paths 250 at closed distance (for example, a flow path opening/closing section 260A for a flow path 250A and the flow path opening/closing section 270B for a flow path 250B) are formed as second middle layer and third middle layer.

Herein, FIGS. 1 to 4 explain a case where the flow path opening/closing sections 141, 142 are formed on a lower layer relatively to the flow paths 131, 132 etc. That is, the microchip 100 disclosed in FIGS. 1 to 4 is a microchip 100 consisting of the third elastic sheet 113 superposed on the fourth elastic sheet 114, the second elastic sheet 112 superposed on the third elastic sheet 113, and the first elastic sheet 111 superposed on the second elastic sheet 112, and the first middle layer, such as flow paths 131, 132, is formed between the first elastic sheet 111 and the second elastic sheet 112. However, relationship in vertical position of each middle layer may be modified freely.

Figure 13:
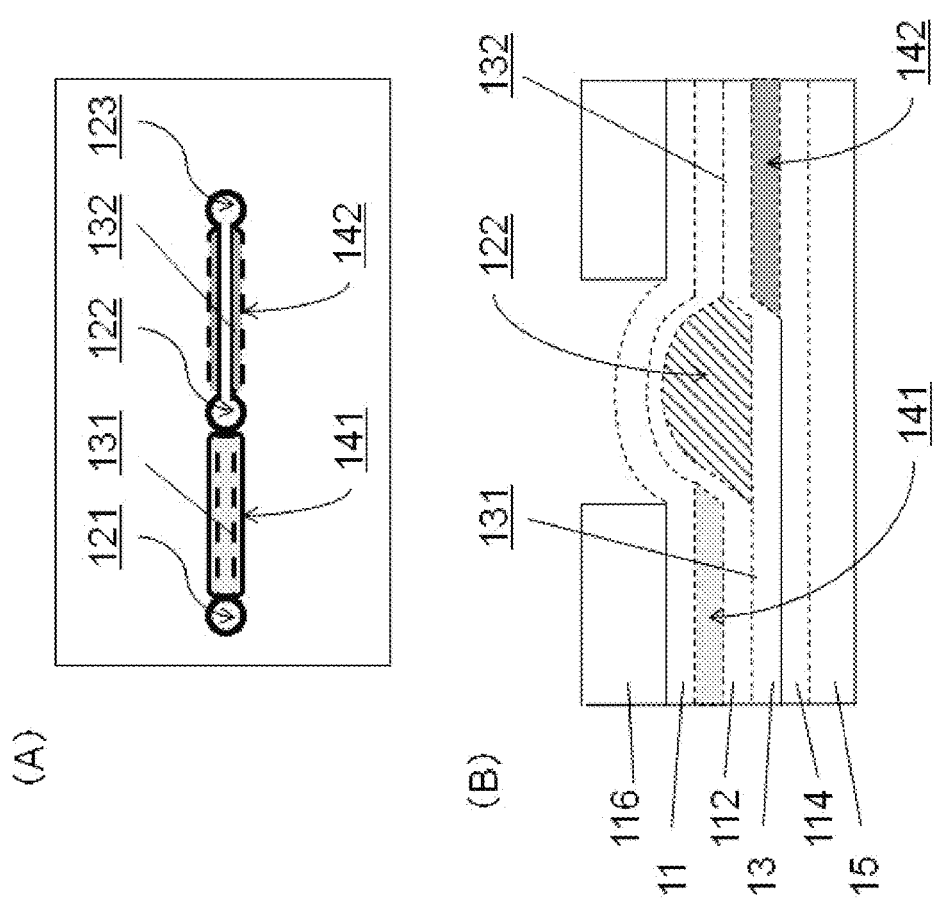
FIG. 13 is an exemplary view showing a modified mode of a microchip 100.

For example, as shown in FIGS. 13A, B, the first middle layer, such as the flow paths 131, 132, may be arranged between the second elastic sheet 112 and the third elastic sheet 113. In other words, flow paths 131, 132 etc. may be constructed in a sandwiched manner between the flow path opening/closing sections 141, 142.

Figure 14:
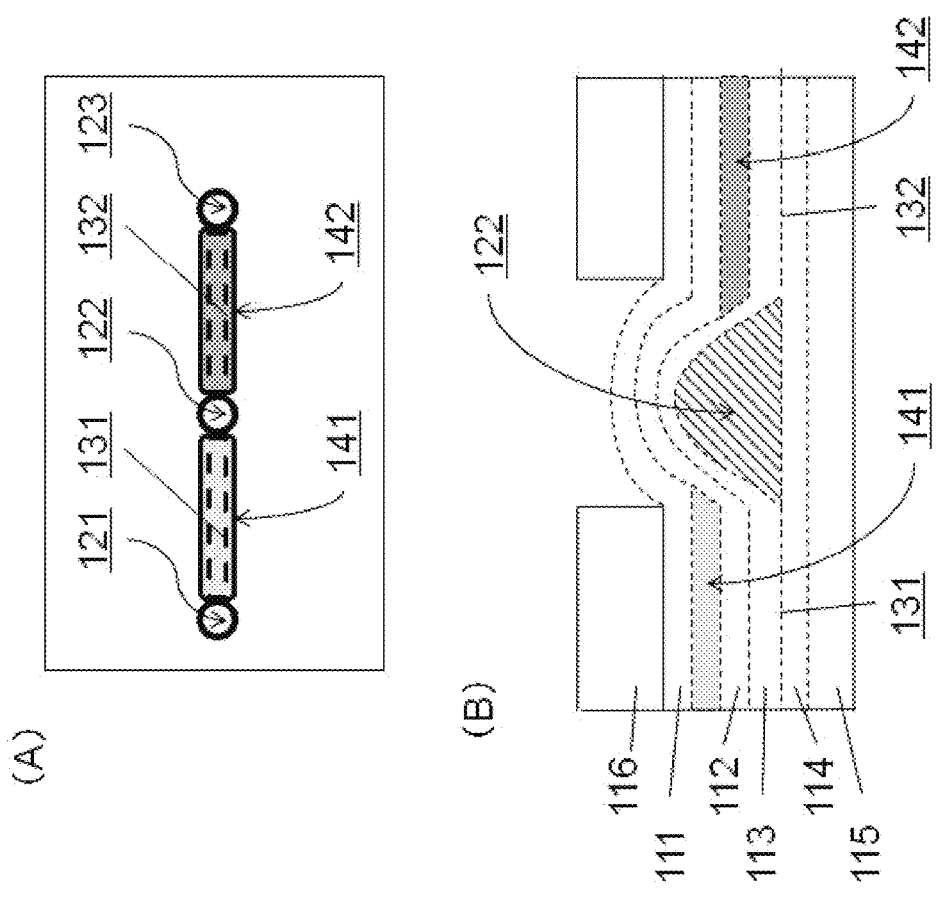
FIG. 14 is an exemplary view showing a modified mode of a microchip 100.

Or, as shown in FIGS. 14A, B, the first middle layer may be arranged between the third elastic sheet 113 and the fourth elastic sheet 114. In other words, the flow path 131, 132 etc. may be formed on lower layer relatively to the flow path opening/closing sections 141, 142. Herein, in FIG. 13A and FIG. 14A, broken line means a construction arranged on lower layer relatively to a construction indicated with full line.

Figure 15:
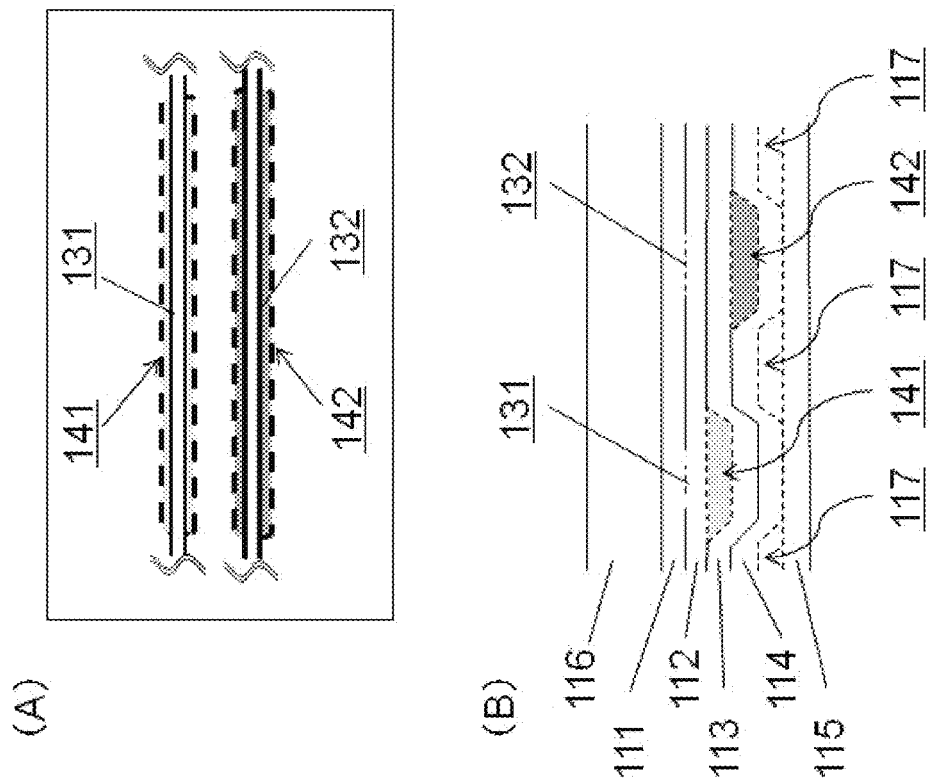
FIG. 15 is an exemplary view showing a modified mode of a microchip 100.

Furthermore, effects disclosed in the present application may be exerted at a concentrated site of a plurality of flow paths and a confluence site of a plurality of flow paths. For example, as shown in FIG. 15, in a case where there are flow paths 131, 132 running in parallel at closed distance, a flow path opening/closing section 141 for the flow path 131 is formed as the second middle layer and a flow path opening/closing section 142 for the flow path 132 is formed as the third middle layer. Thereby, the possibility that the flow path opening/closing section 141, 142 are to be communicated is reduced.

Figure 16:
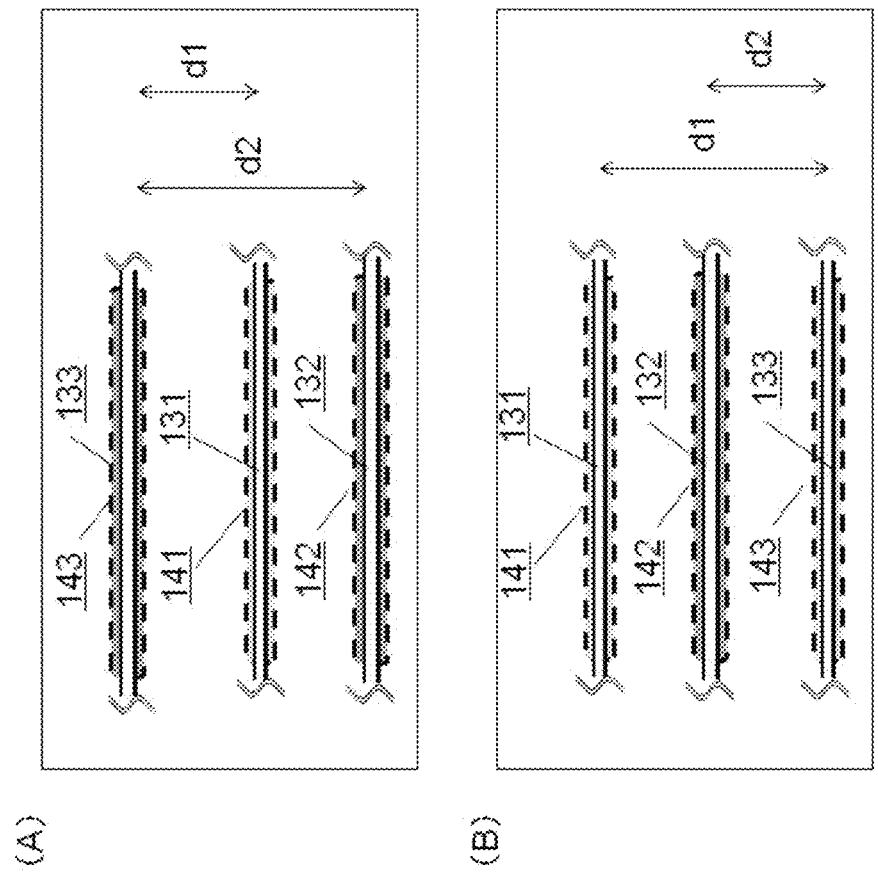
FIG. 16 is an exemplary view showing a modified mode of a microchip 100.

In addition, in a case where further flow path 133 is added, a further flow path opening/closing section 143 may be formed as a middle layer according to the minimum distance between the flow path 131 and the flow path 133 as well as the minimum distance between the flow path 132 and the flow path 133. Specifically, as shown in FIG. 16A, in a case where the minimum distance d1 between the flow path 131 and the flow path 133 is shorter than the minimum distance d2 between the flow path 132 and the flow path 133, the flow path opening/closing section 141 for the flow path 131 is formed as the second middle layer, and the flow path opening/closing section 142 for the flow path 132 and the flow path opening/closing section 143 for the flow path 133 are formed as the third middle layer. In addition, as shown in FIG. 16B, the minimum distance between the flow path 131 and the flow path 133 is longer than the minimum distance between the flow path 132 and the flow path 133, the flow path opening/closing section 141 for the flow path 131 and the flow path opening/closing section 143 for the flow path 133 are formed as the second middle layer, and the flow path opening/closing section 142 for the flow path 132 is formed as the third middle layer. Herein, in a case where the minimum distance d1 between the flow path 131 and the flow path 133 and the minimum distance d2 between the flow path 132 and the flow path 133 is predetermined value or less, the flow path opening/closing section 143 may be formed as a fourth middle layer provided by laminating a fifth elastic sheet.

Figure 17:
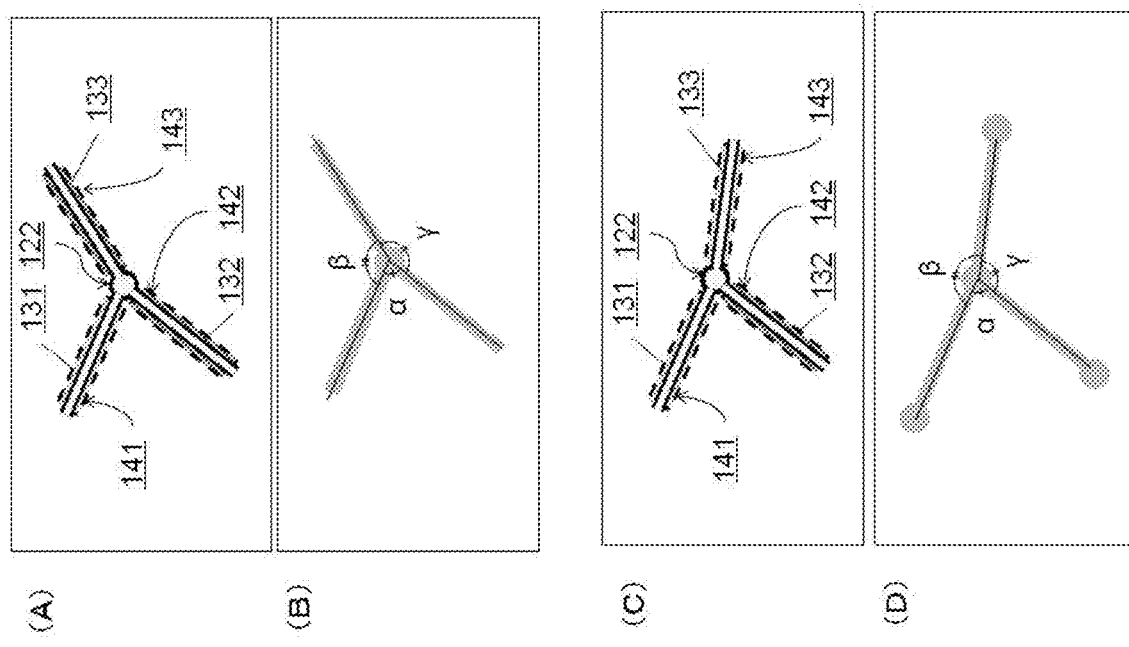
FIG. 17 is an exemplary view showing a modified mode of a microchip 100.
Figure 18:
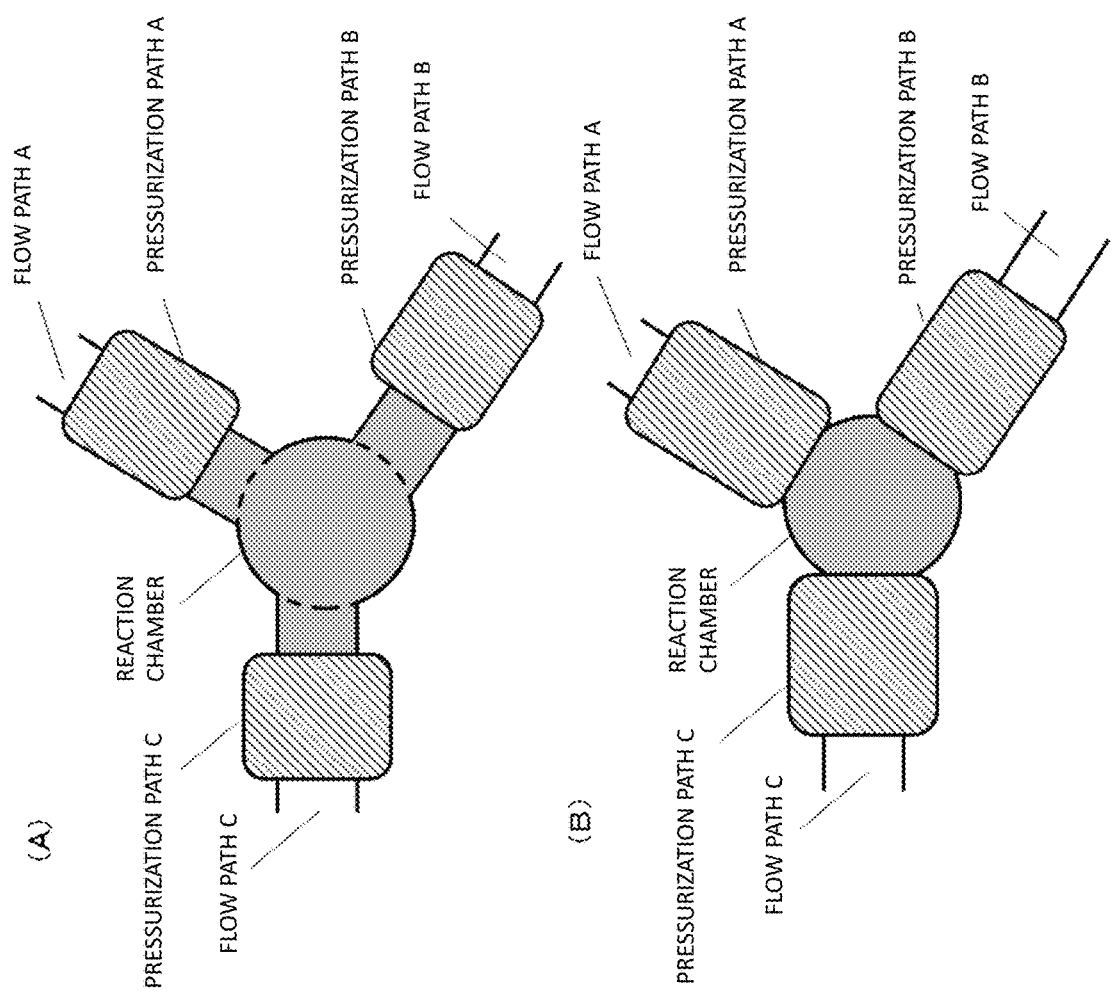
FIG. 18 is an explanatory view of a problem in technology disclosed in Patent Literature 1.
Figure 19:
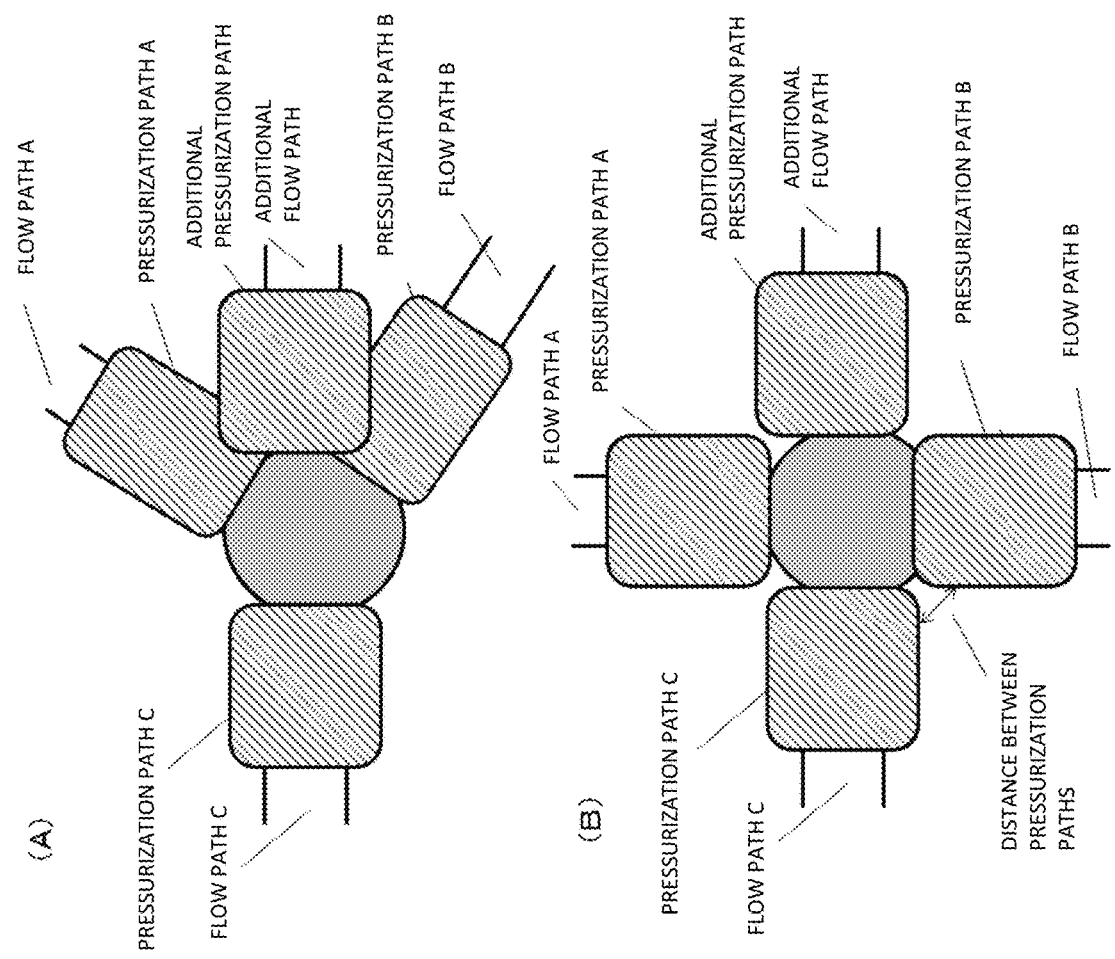
FIG. 19 is an explanatory view of a problem in technology disclosed in Patent Literature 1.

In addition, further flow path 133 is connected to the liquid chamber 122 to which flow paths 131, 132 have been connected, each of flow paths 131 to 133 are radially connected to the liquid chamber and the flow path opening/closing sections 141 to 143 may be formed as middle layers according to the degrees of minor angle between the flow paths. Specifically, as shown in FIGS. 17A, B, in a case where the minor angle ($\alpha$) between the flow path 131 and the flow path 132 is the smallest and the minor angle ($\beta$) between the flow path 131 and the flow path 133 is smaller than the minor angle ($\gamma$) between the flow path 132 and the flow path 133, the flow path opening/closing section 141 for the flow path 131 is formed as second middle layer, and the flow path opening/closing section 142 for the flow path 132 and the flow path opening/closing section 143 for the flow path 133 are formed as the third middle layer. In addition, as shown in FIGS. 17C, D, in a case where the minor angle ($\beta$) between the flow path 131 and the flow path 133 is larger than the minor angle ($\gamma$) between the flow path 132 and the flow path 133, the flow path opening/closing section 141 for the flow path 131 and the flow path opening/closing section 143 for the flow path 133 are formed as the second middle layer, and the flow path opening/closing section 142 for the flow path 132 is formed as the third middle layer. Herein, in a case where the minor angle ($\beta$) between the flow path 131 and the flow path 133 and the minor angle ($\gamma$) between the flow path 132 and the flow path 133 is predetermined value or less, the flow path opening/closing section 143 may be formed as a fourth middle layer provided by laminating a fifth elastic sheet.

A part or all of embodiments disclosed above may be described as following modes, but not limited thereto.

(Mode 1)
A microchip comprising a plurality of laminated elastic sheets, wherein the elastic sheets are partially inadhesive each other so that at least 3 middle layers are formed;
as a first middle layer, first flow path and second flow path through which liquid flows are formed;
as a second middle layer, a first flow path opening/closing section for opening and closing the first flow path is formed; and
as a third middle layer, a second flow path opening/closing section for opening and closing the second flow path is formed.

(Mode 2)
The microchip according to Mode 1, wherein
the first flow path opening/closing section and the second flow path opening/closing section respectively expand to close a corresponding flow path when medium is injected thereinto; and respectively shrink to open a corresponding flow path when the injected medium is released.

(Mode 3)
The microchip according to Mode 1 or 2, wherein
the first middle layer is formed upward in lamination direction from the second middle layer and the third middle layer.

(Mode 4)
The microchip according to Mode 1 or 2, wherein
the first middle layer is formed between the second middle layer and the third middle layer.

(Mode 5)
The microchip according to Mode 1 or 2, wherein
the first middle layer is formed downward in lamination direction from the second middle layer and the third middle layer.

(Mode 6)
The microchip according to any of Modes 1 to 5, wherein
the first flow path and the second flow path are formed in a manner that they run in parallel each other.

(Mode 7)
The microchip according to any of Modes 1 to 6, wherein
as a first middle layer, third flow path is formed;
a third flow path opening/closing section for opening and closing the third flow path is formed as a middle layer according to a minimum distance d1 between the first flow path and the third flow path, and a minimum distance d2 between the second flow path and the third flow path.

(Mode 8)
The microchip according to Mode 7, wherein
the first flow path, the second flow path and the third flow path are formed in a manner that the first flow path and the second flow path is closest, and
the third flow path opening/closing section is formed as the third middle layer in a case where the minimum distance d1 between the first flow path and the third flow path is shorter than the minimum distance d2 between the second flow path and the third flow path; and the third flow path opening/closing section is formed as the second middle layer in a case where the minimum distance d1 between the first flow path and the third flow path is longer than the minimum distance d2 between the second flow path and the third flow path.

(Mode 9)
The microchip according to Mode 7, wherein
the third flow path opening/closing section is formed as a fourth middle layer in a case where the minimum distance d1 between the first flow path and the third flow path as well as the minimum distance d2 between the second flow path and the third flow path are a predetermined value or less.

(Mode 10)
The microchip according to any of Modes 1 to 5, wherein a liquid chamber in which liquid is stored is formed as the first middle layer, and
respective one end of the first flow path and the second flow path is connected to the same liquid chamber.

(Mode 11)
The microchip according to any of Modes 1 to 5, wherein the third flow path is formed as the first middle layer;
the first flow path, the second flow path and the third flow path are radially connected to the same liquid chamber; and
the third flow path opening/closing section for opening and closing the third flow path is formed as a middle layer according to degrees of minor angle β between the first flow path and the third flow path, as well as degrees of minor angle γ between the second flow path and the third flow path.

(Mode 12)
The microchip according to Mode 11, wherein
minor angle α between the first flow path and the second flow path is the smallest;
the third flow path opening/closing section is formed as the third middle layer in a case where the minor angle β between the first flow path and the third flow path is smaller than the minor angle γ between the second flow path and the third flow path; and the third flow path opening/closing section is formed as the second middle layer in a case where the minor angle β between the first flow path and the third flow path is larger than the minor angle γ between the second flow path and the third flow path.

(Mode 13)
The microchip according to Mode 11, wherein
the third flow path opening/closing section is formed as fourth middle layer in a case where the degrees of the minor angle β between the first flow path and the third flow path as well as the degrees of the minor angle γ between the second flow path and the third flow path are a predetermined value or less.

(Mode 14)
A microchip controlling method, controlling a microchip which comprises a plurality of laminated elastic sheets;
in which the elastic sheets are partially inadhesive each other so that at least 3 middle layers are formed;
in which, as a first middle layer, first flow path and second flow path through which liquid flows are formed;
in which, as a second middle layer, a first flow path opening/closing section for opening and closing the first flow path is formed; and
in which, as a third middle layer, a second flow path opening/closing section for opening and closing the second flow path is formed;
wherein, when liquid flows through the first flow path, medium is released from the first flow path opening/closing section so that the first flow path opening/closing section shrinks in order to open the first flow path, and medium is injected into the second flow path opening/closing section so that the second flow path opening/closing section is expanded in order to close the second flow path.

(Mode 15)
A microchip controlling apparatus controlling a microchip which comprises a plurality of laminated elastic sheets;

in which the elastic sheets are partially inadhesive each other so that at least 3 middle layers are formed;

in which, as a first middle layer, a first flow path and second flow path through which liquid flows are formed;

in which, as a second middle layer, a first flow path opening/closing section for opening and closing the first flow path is formed; and in which, as a third middle layer, a second flow path opening/closing section for opening and closing the second flow path is formed;

wherein, when liquid flows through the first flow path, medium is released from the first flow path opening/closing section so that the first flow path opening/closing section shrinks in order to open the first flow path, and medium is injected into the second flow path opening/closing section so that the second flow path opening/closing section is expanded in order to close the second flow path.

The particular exemplary embodiments or examples may be modified or adjusted within the scope of the entire disclosure of the present invention, inclusive of claims, based on the fundamental technical concept of the invention. In addition, a variety of combinations or selection of elements disclosed herein, inclusive each element in each claim, each element in each example, each element in each drawing etc., may be made within the context of entire disclosure of the present inventions. That is, the present invention may cover a wide variety of modifications or corrections that may be made by those skilled in the art in accordance with the entire disclosure of the present invention, inclusive of claims, and the technical concept of the present invention.

REFERENCE SIGNS LIST 10 microchip controlling apparatus
11 base station
12 table
13 temperature control unit
14 electrophoresis unit
15 lid
16 hinge
17A, B pins
18 electrodes
19, 19A, 19B pressurizing holes
20 O-ring
21 tubes
22 solenoid valve
23 pressure accumulator
24 controller
25 DNA extracting unit
26 power supplying part
27 displaying part
100 microchip
111 (first) elastic sheet
112 (second) elastic sheet
113 (third) elastic sheet
114 (fourth) elastic sheet
115 resin plate
115A, B recessed parts
116 resin plate
116A control hole
117 space part
121 to 123 liquid chambers
131 to 134 flow paths
141 (first) flow path opening/closing section
142 (second) flow path opening/closing section
143 flow path opening/closing section
144 flow path opening/closing section
200 microchip
211 (first) elastic sheet
212 (second) elastic sheet
213 (third) elastic sheet
214 (fourth) elastic sheet
215 resin plate
216 resin plate
217A, B pin holes
219 electrode holes
220A, B medium charging/discharging hole
240 DNA extraction/PCR section
240A, B liquid chambers
241 sample solution injection section
241A cover film
242 wash buffer injection section
243 elution buffer injection section
244 DNA extracting section
245 PCR section
246 denaturation section
247 volume determination section
248 confluence point
249 branching point
250A to J, X, Y, Z flow paths
260A, C, E, G, I, Y (on second middle layer) flow path opening/closing section
261A medium flow path
270B, D, F, H, X, Z (on third middle layer) flow path opening/closing section
271B medium flow path
280 electrophoresis section
281 sample flow path
282 capillary
283 polymer injection section
284A to C electrode chambers
284D reservoir
285 bridging flow path
290 space part

What is claimed is:

1. A microchip adapted to carry out a biochemical reaction, wherein
the microchip comprises at least 4 laminated elastic sheets which are partially inadhesive to each other so that at least 3 middle layers are formed;
in a first middle layer, a first flow path, second flow path and third flow path which are separated by adhesive section from each other and through which liquid flows are formed;
in a second middle layer, a first flow path opening/closing section for opening and closing the first flow path is formed;
in a third middle layer, a second flow path opening/closing section for opening and closing the second flow path is formed;
in any one of the second middle layer or third middle layer, a third flow path opening/closing section for opening and closing the third flow path is formed, wherein the second middle layer or third middle layer is selected based on a minimum distance d1 between the first flow path and the third flow path and a minimum distance d2 between the second flow path and the third flow path; and
the first flow path opening/closing section, the second flow path opening/closing section, and the third flow path opening/closing section respectively expand to close a corresponding flow path when medium is injected thereinto; and respectively shrink to open a corresponding flow path when the injected medium is released.

2. The microchip according to claim 1, wherein
the 4 laminated elastic sheets comprise a fourth elastic sheet, a third elastic sheet superposed on the fourth elastic sheet, a second elastic sheet superposed on the third elastic sheet, a first elastic sheet superposed on the second elastic sheet; and wherein
a middle layer formed by making the first elastic sheet and the second elastic sheet partially inadhesive corresponds to the first middle layer;
a middle layer formed by making the second elastic sheet and the third elastic sheet partially inadhesive corresponds to either of the second middle layer or the third middle layer; and
a middle layer formed by making the third elastic sheet and the fourth elastic sheet partially inadhesive corresponds to the any one of the second middle layer or the third middle layer.

3. The microchip according to claim 1, wherein
the first middle layer is formed between the second middle layer and the third middle layer.

4. The microchip according to claim 1, wherein
the 4 laminated elastic sheets comprise a fourth elastic sheet, a third elastic sheet superposed on the fourth elastic sheet, a second elastic sheet superposed on the third elastic sheet, a first elastic sheet superposed on the second elastic sheet; and wherein
a middle layer formed by making the first elastic sheet and the second elastic sheet partially inadhesive corresponds to any one of the second middle layer or the third middle layer;
a middle layer formed by making the second elastic sheet and the third elastic sheet partially inadhesive corresponds to the other one of the second middle layer or the third middle layer; and
a middle layer formed by making the third elastic sheet and the fourth elastic sheet partially inadhesive corresponds to the first middle layer.

5. The microchip according to claim 1, wherein
the first flow path, the second flow path and the third flow path are formed in a manner that they run in parallel each other.

6. The microchip according to claim 1, wherein
under the first flow path is closer to the second flow path than the third flow path and the second flow path is closer to the first flow path than the third flow path; and
the third flow path opening/closing section is formed in the third middle layer in a case where the minimum distance d1 between the first flow path and the third flow path is shorter than the minimum distance d2 between the second flow path and the third flow path; or
the third flow path opening/closing section is formed in the second middle layer in a case where the minimum distance d1 between the first flow path and the third flow path is longer than the minimum distance d2 between the second flow path and the third flow path.

7. The microchip according to claim 1, wherein
the microchip further comprises a fifth elastic sheet;
the third flow path opening/closing section is formed in a fourth middle layer which is formed by making any one of the 4 elastic sheets and the fifth elastic sheet partially inadhesive in a case where the minimum distance d1 between the first flow path and the third flow path as well as the minimum distance d2 between the second flow path and the third flow path are a threshold or less.

8. A microchip adapted to carry out a biochemical reaction, wherein
the microchip comprises at least 4 laminated elastic sheets which are partially inadhesive to each other so that at least 3 middle layers are formed;
in a first middle layer, a first flow path, second flow path and third flow path which are separated by adhesive section from each other and through which liquid flows, as well as a liquid chamber in which liquid is stored are formed;
in a second middle layer, a first flow path opening/closing section for opening and closing the first flow path is formed;
in a third middle layer, a second flow path opening/closing section for opening and closing the second flow path is formed;
the first flow path, the second flow path and the third flow path are radially connected to the same liquid chamber;
in any one of the second middle layer or third middle layer, a third flow path opening/closing section for opening and closing the third flow path is formed, wherein the second middle layer or third middle layer is selected based on degrees of a minor angle $\beta$ between the first flow path and the third flow path, as well as degrees of a minor angle $\gamma$ between the second flow path and the third flow path; and
the first flow path opening/closing section, the second flow path opening/closing section, and the third flow path opening/closing section respectively expand to close a corresponding flow path when medium is injected thereinto; and respectively shrink to open a corresponding flow path when the injected medium is released.

9. The microchip according to claim 8, wherein
a minor angle $\alpha$ between the first flow path and the second flow path is at the smallest;
the third flow path opening/closing section is formed in the third middle layer in a case where the minor angle $\beta$ between the first flow path and the third flow path is smaller than the minor angle $\gamma$ between the second flow path and the third flow path; or
the third flow path opening/closing section is formed in the second middle layer in a case where the minor angle $\beta$ between the first flow path and the third flow path is larger than the minor angle $\gamma$ between the second flow path and the third flow path.

10. The microchip according to claim 8, wherein
the microchip further comprises a fifth elastic sheet;
the third flow path opening/closing section is formed in fourth middle layer which is formed by making any one of the 4 elastic sheets and the fifth elastic sheet partially inadhesive in a case where the degrees of the minor angle $\beta$ between the first flow path and the third flow path as well as the degrees of the minor angle $\gamma$ between the second flow path and the third flow path are a threshold or less.

11. A microchip controlling apparatus controlling a microchip adapted to carry out a biochemical reaction, wherein
the microchip comprises at least 4 laminated elastic sheets;
in which the elastic sheets are partially inadhesive to each other so that at least 3 middle layers are formed;

in which, in a first middle layer, a first flow path, second flow path and third flow path which are separated by adhesive section from each other and through which liquid flows are formed;

in which, in a second middle layer, a first flow path opening/closing section for opening and closing the first flow path is formed;

in which, in a third middle layer, a second flow path opening/closing section for opening and closing the second flow path is formed;

in which, in either of the second middle layer or third middle layer, a third flow path opening/closing section for opening and closing the third flow path is formed, wherein the second middle layer or third middle layer is selected based on a minimum distance d1 between the first flow path and the third flow path and a minimum distance d2 between the second flow path and the third flow path; or in either of the second middle layer or third middle layer, a third flow path opening/closing section for opening and closing the third flow path is formed, wherein the second middle layer or third middle layer is selected based on degrees of a minor angle β between the first flow path and the third flow path, as well as degrees of a minor angle γ between the second flow path and the third flow path; and wherein the microchip controlling apparatus is configured to conduct a control such that when liquid flows through the first flow path, medium is released from the first flow path opening/closing section so that the first flow path opening/closing section shrinks in order to open the first flow path, and medium is injected into the second flow path opening/closing section and the third flow path opening/closing section so that the second flow path opening/closing section is expanded in order to close the second flow path and the third flow path.

12. The microchip according to claim 8, wherein
the 4 laminated elastic sheets comprise a fourth elastic sheet, a third elastic sheet superposed on the fourth elastic sheet, a second elastic sheet superposed on the third elastic sheet, a first elastic sheet superposed on the second elastic sheet; and wherein a middle layer formed by making the first elastic sheet and the second elastic sheet partially inadhesive corresponds to the first middle layer;

a middle layer formed by making the second elastic sheet and the third elastic sheet partially inadhesive corresponds to either of the second middle layer or the third middle layer; and a middle layer formed by making the third elastic sheet and the fourth elastic sheet partially inadhesive corresponds to the any one of the second middle layer or the third middle layer.

13. The microchip according to claim 8, wherein
the first middle layer is formed between the second middle layer and the third middle layer.

14. The microchip according to claim 8, wherein
the 4 laminated elastic sheets comprise a fourth elastic sheet, a third elastic sheet superposed on the fourth elastic sheet, a second elastic sheet superposed on the third elastic sheet, a first elastic sheet superposed on the second elastic sheet; and wherein a middle layer formed by making the first elastic sheet and the second elastic sheet partially inadhesive corresponds to any one of the second middle layer or the third middle layer;

a middle layer formed by making the second elastic sheet and the third elastic sheet partially inadhesive corresponds to the other one of the second middle layer or the third middle layer; and a middle layer formed by making the third elastic sheet and the fourth elastic sheet partially inadhesive corresponds to the first middle layer.

* * * * *